US009623563B2

(12) United States Patent
Nixon

(10) Patent No.: US 9,623,563 B2
(45) Date of Patent: *Apr. 18, 2017

(54) TOOL GRIP CALIBRATION FOR ROBOTIC SURGERY

(71) Applicant: Intuitive Surgical Operations, Inc., Sunnyvale, CA (US)

(72) Inventor: Tom Nixon, Santa Clara, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/748,647

(22) Filed: Jun. 24, 2015

(65) Prior Publication Data

US 2015/0314451 A1 Nov. 5, 2015

Related U.S. Application Data

(63) Continuation of application No. 14/272,862, filed on May 8, 2014, now Pat. No. 9,085,083, which is a
(Continued)

(51) Int. Cl.
*G06F 19/00* (2011.01)
*B25J 9/16* (2006.01)
(Continued)

(52) U.S. Cl.
CPC ............. *B25J 9/1692* (2013.01); *A61B 34/30* (2016.02); *A61B 34/35* (2016.02); *A61B 34/37* (2016.02);
(Continued)

(58) Field of Classification Search
CPC .... B25J 9/1692; A61B 19/2203; A61B 19/46; A61B 2019/223; A61B 2019/466; G05B 2219/45123; G05B 2219/49305
(Continued)

(56) References Cited

U.S. PATENT DOCUMENTS 3,923,166 A 12/1975 Fletcher et al.
4,150,326 A 4/1979 Engelberger et al.
(Continued)

FOREIGN PATENT DOCUMENTS

DE 4213426 1/1997
WO WO-9216141 A1 10/1992
(Continued)

OTHER PUBLICATIONS

Adams, Ludwig et al., "Computer-Assisted Surgery," IEEE Computer Graphics & Applications, May 1990, pp. 43-52, vol. 10—Issue 3, IEEE Computer Society Press.
(Continued)

*Primary Examiner* — McDieunel Marc

(57) ABSTRACT

Telerobotic, telesurgical, and surgical robotic devices, systems, and methods selectively calibrate end effector jaws by bringing the jaw elements into engagement with each other. Commanded torque signals may bring the end effector elements into engagement while monitoring the resulting position of a drive system, optionally using a second derivative of the torque/position relationship so as to identify an end effector engagement position. Calibration can allow the end effector engagement position to correspond to a nominal closed position of an input handle by compensating for wear on the end effector, the end effector drive system, then manipulator, the manipulator drive system, the manipulator/ end effector interfacing, and manufacturing tolerances.

17 Claims, 13 Drawing Sheets

Related U.S. Application Data continuation of application No. 13/873,363, filed on Apr. 30, 2013, now Pat. No. 8,761,930, which is a continuation of application No. 13/246,421, filed on Sep. 27, 2011, now Pat. No. 8,452,447, which is a continuation of application No. 11/972,771, filed on Jan. 11, 2008, now Pat. No. 9,317,651, which is a continuation of application No. 10/839,805, filed on May 4, 2004, now Pat. No. 7,386,365.

(51) Int. Cl.

| | | |
|---|---|---|
| *A61B 34/00* | (2016.01) | |
| *A61B 34/30* | (2016.01) | |
| *A61B 34/37* | (2016.01) | |
| *A61B 34/35* | (2016.01) | |
| *A61B 17/00* | (2006.01) | |
| *A61B 17/29* | (2006.01) | |
| *A61B 90/00* | (2016.01) | |

(52) U.S. Cl.
CPC ............. *A61B 34/70* (2016.02); *A61B 34/71* (2016.02); *A61B 90/06* (2016.02); *A61B 17/29* (2013.01); *A61B 90/361* (2016.02); *A61B 2017/00017* (2013.01); *A61B 2017/00207* (2013.01); *A61B 2017/00477* (2013.01); *A61B 2017/00725* (2013.01); *A61B 2034/305* (2016.02); *A61B 2090/066* (2016.02); *G05B 2219/45123* (2013.01); *G05B 2219/49305* (2013.01); *Y10S 901/39* (2013.01); *Y10S 901/40* (2013.01); *Y10S 901/44* (2013.01); *Y10S 901/45* (2013.01); *Y10S 901/46* (2013.01)

(58) Field of Classification Search
USPC ......... 700/45, 245, 247, 248, 251, 254, 259, 700/260, 261, 262, 263, 264; 901/8, 9, 901/14, 15, 21, 22, 24, 29, 30, 34, 36, 39, 901/40, 44, 45, 46, 48; 414/4, 5, 729, 414/730, 735, 744.5; 318/568.1, 568.11, 318/568.12, 568.18, 568.21, 568.24, 646; 128/897; 294/907; 74/479.01; 606/130; 623/62; 244/172.5
See application file for complete search history.

(56) References Cited

U.S. PATENT DOCUMENTS

| | | |
|---|---|---|
| 4,281,447 A | 8/1981 | Miller et al. |
| 4,332,066 A | 6/1982 | Hailey et al. |
| 4,349,837 A | 9/1982 | Hinds |
| 4,472,668 A | 9/1984 | Mutschler et al. |
| 4,486,928 A | 12/1984 | Tucker et al. |
| 4,500,065 A | 2/1985 | Hennekes et al. |
| 4,510,574 A | 4/1985 | Guittet et al. |
| 4,512,709 A | 4/1985 | Hennekes et al. |
| 4,696,501 A | 9/1987 | Webb |
| 4,706,372 A | 11/1987 | Ferrero et al. |
| 4,710,093 A | 12/1987 | Zimmer et al. |
| 4,722,056 A | 1/1988 | Roberts et al. |
| 4,762,455 A | 8/1988 | Coughlan et al. |
| 4,793,053 A | 12/1988 | Zuccaro et al. |
| 4,809,747 A | 3/1989 | Choly et al. |
| 4,819,978 A | 4/1989 | Scheinman et al. |
| 4,830,569 A | 5/1989 | Jannborg |
| 4,832,198 A | 5/1989 | Alikhan |
| 4,833,383 A | 5/1989 | Skarr et al. |
| 4,837,734 A | 6/1989 | Ichikawa et al. |
| 4,853,874 A | 8/1989 | Iwamoto et al. |
| 4,860,215 A | 8/1989 | Seraji |
| 4,863,133 A | 9/1989 | Bonnell |
| 4,942,538 A | 7/1990 | Yuan et al. |
| 4,942,539 A | 7/1990 | McGee et al. |
| 4,979,949 A | 12/1990 | Matsen, III |
| 4,989,253 A | 1/1991 | Liang et al. |
| 4,996,975 A | 3/1991 | Nakamura |
| 5,018,266 A | 5/1991 | Hutchinson et al. |
| 5,046,022 A | 9/1991 | Conway et al. |
| 5,078,140 A | 1/1992 | Kwoh |
| 5,143,453 A | 9/1992 | Weynant |
| 5,154,717 A | 10/1992 | Matsen, III et al. |
| 5,174,300 A | 12/1992 | Bales et al. |
| 5,182,641 A | 1/1993 | Diner et al. |
| 5,184,601 A | 2/1993 | Putman |
| 5,187,796 A | 2/1993 | Wang et al. |
| 5,217,003 A | 6/1993 | Wilk |
| 5,221,283 A | 6/1993 | Chang |
| 5,236,432 A | 8/1993 | Matsen, III et al. |
| 5,250,056 A | 10/1993 | Hasson |
| 5,255,429 A | 10/1993 | Nishi et al. |
| 5,257,998 A | 11/1993 | Ota et al. |
| 5,271,384 A | 12/1993 | McEwen et al. |
| 5,279,309 A | 1/1994 | Taylor et al. |
| 5,294,209 A | 3/1994 | Naka et al. |
| 5,299,288 A | 3/1994 | Glassman et al. |
| 5,305,203 A | 4/1994 | Raab |
| 5,312,212 A | 5/1994 | Naumec |
| 5,313,306 A | 5/1994 | Kuban et al. |
| 5,313,935 A | 5/1994 | Kortenbach et al. |
| 5,321,353 A | 6/1994 | Furness |
| 5,339,799 A | 8/1994 | Kami et al. |
| 5,341,950 A | 8/1994 | Sinz |
| 5,343,385 A | 8/1994 | Joskowicz et al. |
| 5,354,162 A | 10/1994 | Burdea et al. |
| 5,354,314 A | 10/1994 | Hardy et al. |
| 5,355,743 A | 10/1994 | Tesar |
| 5,359,993 A | 11/1994 | Slater et al. |
| 5,368,015 A | 11/1994 | Wilk |
| 5,372,147 A | 12/1994 | Lathrop, Jr. et al. |
| 5,382,885 A | 1/1995 | Salcudean et al. |
| 5,397,323 A | 3/1995 | Taylor et al. |
| 5,399,951 A | 3/1995 | Lavallee et al. |
| 5,400,267 A | 3/1995 | Denen et al. |
| 5,402,801 A | 4/1995 | Taylor |
| 5,403,319 A | 4/1995 | Matsen, III et al. |
| 5,417,210 A | 5/1995 | Funda et al. |
| 5,427,097 A | 6/1995 | Depp |
| 5,430,643 A | 7/1995 | Seraji |
| 5,451,368 A | 9/1995 | Jacob |
| 5,503,320 A | 4/1996 | Webster et al. |
| 5,515,478 A | 5/1996 | Wang |
| 5,524,180 A | 6/1996 | Wang et al. |
| 5,553,198 A | 9/1996 | Wang et al. |
| 5,624,398 A | 4/1997 | Smith et al. |
| 5,631,973 A | 5/1997 | Green |
| 5,649,956 A | 7/1997 | Jensen et al. |
| 5,657,429 A | 8/1997 | Wang et al. |
| 5,697,939 A | 12/1997 | Kubota et al. |
| 5,737,500 A | 4/1998 | Seraji et al. |
| 5,754,741 A | 5/1998 | Wang et al. |
| 5,762,458 A | 6/1998 | Wang et al. |
| 5,784,542 A | 7/1998 | Ohm et al. |
| 5,791,231 A | 8/1998 | Cohn et al. |
| 5,792,135 A | 8/1998 | Madhani et al. |
| 5,792,178 A | 8/1998 | Welch et al. |
| 5,797,900 A | 8/1998 | Madhani et al. |
| 5,800,423 A | 9/1998 | Jensen |
| 5,802,201 A | 9/1998 | Nayar et al. |
| 5,807,377 A | 9/1998 | Madhani et al. |
| 5,808,665 A | 9/1998 | Green |
| 5,810,880 A | 9/1998 | Jensen et al. |
| 5,814,038 A | 9/1998 | Jensen et al. |
| 5,815,640 A | 9/1998 | Wang et al. |
| 5,820,545 A | 10/1998 | Arbter et al. |
| 5,841,950 A | 11/1998 | Wang et al. |
| 5,855,553 A | 1/1999 | Tajima et al. |
| 5,855,583 A | 1/1999 | Wang et al. |
| 5,859,934 A | 1/1999 | Green |
| 5,876,325 A | 3/1999 | Mizuno et al. |
| 5,878,193 A | 3/1999 | Wang et al. |

(56) References Cited

U.S. PATENT DOCUMENTS

| | | | |
|---|---|---|---|
| 5,907,664 | A | 5/1999 | Wang et al. |
| 5,911,036 | A | 6/1999 | Wright et al. |
| 5,931,832 | A | 8/1999 | Jensen |
| 5,950,629 | A | 9/1999 | Taylor et al. |
| 5,971,976 | A | 10/1999 | Wang et al. |
| 5,976,156 | A | 11/1999 | Taylor et al. |
| 6,024,695 | A | 2/2000 | Taylor et al. |
| 6,113,395 | A | 9/2000 | Hon |
| 6,132,368 | A | 10/2000 | Cooper |
| 6,165,184 | A | 12/2000 | Verdura et al. |
| 6,219,589 | B1 | 4/2001 | Faraz et al. |
| 6,223,100 | B1 | 4/2001 | Green |
| 6,228,097 | B1 | 5/2001 | Levinson et al. |
| 6,231,526 | B1 | 5/2001 | Taylor et al. |
| 6,244,809 | B1 | 6/2001 | Wang et al. |
| 6,280,458 | B1 | 8/2001 | Boche et al. |
| 6,312,435 | B1 | 11/2001 | Wallace et al. |
| 6,323,837 | B1 | 11/2001 | Rosenberg |
| 6,325,808 | B1 | 12/2001 | Bernard et al. |
| 6,331,181 | B1 | 12/2001 | Tierney et al. |
| 6,424,885 | B1 | 7/2002 | Niemeyer et al. |
| 6,436,107 | B1 | 8/2002 | Wang et al. |
| 6,459,926 | B1 | 10/2002 | Nowlin et al. |
| 6,587,750 | B2 | 7/2003 | Gerbi et al. |
| 6,620,173 | B2 | 9/2003 | Gerbi et al. |
| 6,659,939 | B2 | 12/2003 | Moll et al. |
| 6,764,445 | B2 | 7/2004 | Ramans et al. |
| 6,837,883 | B2 | 1/2005 | Moll et al. |
| 7,087,049 | B2 | 8/2006 | Nowlin et al. |
| 7,155,316 | B2 | 12/2006 | Sutherland et al. |
| 7,373,219 | B2 | 5/2008 | Nowlin et al. |
| 7,379,790 | B2 | 5/2008 | Toth et al. |
| 7,386,365 | B2 | 6/2008 | Nixon |
| 7,607,440 | B2 | 10/2009 | Coste-Maniere et al. |
| 7,865,266 | B2 | 1/2011 | Moll et al. |
| 8,452,447 | B2 * | 5/2013 | Nixon .................... A61B 19/22 700/245 |
| 8,761,930 | B2 | 6/2014 | Nixon |
| 9,085,083 | B2 | 7/2015 | Nixon |
| 2001/0018591 | A1 | 8/2001 | Brock et al. |
| 2001/0056283 | A1 | 12/2001 | Carter et al. |
| 2002/0042620 | A1 | 4/2002 | Julian et al. |
| 2002/0058929 | A1 | 5/2002 | Green |
| 2003/0195664 | A1 | 10/2003 | Nowlin et al. |
| 2005/0067459 | A1 | 3/2005 | Swayze et al. |
| 2008/0114494 | A1 | 5/2008 | Nixon |
| 2008/0221732 | A1 | 9/2008 | Toth et al. |
| 2011/0301754 | A1 | 12/2011 | Toth et al. |

FOREIGN PATENT DOCUMENTS

| | | |
|---|---|---|
| WO | WO-9313916 A1 | 7/1993 |
| WO | WO-9426167 A1 | 11/1994 |
| WO | WO-9501757 A1 | 1/1995 |
| WO | WO-9516396 A1 | 6/1995 |
| WO | WO-9530964 A1 | 11/1995 |
| WO | WO-9639944 A1 | 12/1996 |
| WO | WO-9950721 A1 | 10/1999 |
| WO | WO-0141052 A1 | 6/2001 |
| WO | WO-03049596 A2 | 6/2003 |
| WO | WO-03049910 A2 | 6/2003 |

OTHER PUBLICATIONS

Alexander, Arthur D. III, "Impacts of Telemation on Modern Society," Symposium on Theory and Practice of Robots and Manipulators, Centre for Mechanical Sciences 1st CISM IFToMM Symposium, Sep. 5-8, 1974, pp. 121-136, vol. 2, Springer-Verlag.
Arai, Tatsuo et al., "Bilateral control for manipulators with different configurations," IECON Inn Conference on Industrial Electronics Control and Instrumentation, Oct. 22-26, 1984, pp. 40-45, vol. 1.
Bauer, W. et al., "Virtual reality as interface for interaction and manipulation in endoscopy," Minimally Invasive Therapy, 1995, pp. 319-339, vol. 4, Blackwell Science Ltd.
Bejczy, Antal K. et al., "Controlling Remote Manipulators through Kinesthetic Coupling," Computers in Mechanical Engineering, 1983, pp. 48-60, vol. 1—Issue 1.
Bergamasco M., et al., "Advanced Interfaces for Teleoperated Biomedical Robots," IEEE Engineering in Medicine & Biology Society 11th Annual Int'l Conf., pp. 912-913, vol. 3, IEEE, Jun. 1989.
Bluethmann, B et al., "Experiments in Dexterous Hybrid Force and Position Control of Master/Slave Electrohydraulic Manipulator," in Proceedings of the 1995 IEEE/RSJ International Conference on Intelligent Robots and Systems, Aug. 5-9, 1995, pp. 27-32, vol. 3, IEEE Computer Society.
Borovoi, A.V., "Stability of a manipulator with force feedback," Izv. AN SSSR Mekhanika Tverdogo Teal, 1990, pp. 37-45, vol. 25—Issue 1, Allerton Press, Inc.
Bowersox, Jon C. et al., "Vascular applications of telepresence surgery: Initial feasibility studies in swine," J. Vascular Surgery, Feb. 1996, pp. 281-287, vol. 23—Issue 2.
Burdea, Grigore et al., "Dextrous Telerobotics with Force Feedback—an overview. Part 2: Control and Implementation," Robotica, 1991, pp. 291-298, vol. 9.
Butner, Steven E. et al., "A real-time system for tele-surgery," IEEE 21st International Conference on Distributed Computing Systems, 2001, pp. 236-243, IEEE.
Cavusoglu, Murat Cenk et al., "A Laparoscopic Telesurgical Workstation," IEEE Transactions on Robotics and Automation, Aug. 1999, vol. 15, Issue 4, pp. 728-739.
Cohn, Michael C., "Medical Robotics," http://www-bsac.eecs.berkeley.edu/, 1996, pp. 1-8 and 4.
Colgate, Edward, J., "Power and Impedance Scaling in Bilateral Manipulation," IEEE International Conference on Robotics and Automation, Sacramento, California, Apr. 1991, pp. 2292-2297, vol. 3, IEEE.
Fischer, Harald et al., "Tactile Feedback for Endoscopic Surgery," Interactive Technology and the New Paradigm for Healthcare, 1995, pp. 114-117, vol. 19, IOS Press and Ohmsha.
Fisher, Scott S., "Virtual interface environment," IEEE/AIAA 7th Digital Avionics Systems Conference Ft. Worth Texas, 1986, pp. 346-350, IEEE.
Fu, K.S. et al., "Robotics: control, sensing, vision, and intelligence," 1987, pp. 12-76 and 201-265, Ch. 2 & 5, McGraw-Hill Book Company.
Fukuda, Toshio et al., "A new method of master-slave type of teleoperation for a micro-manipulator system," IEEE Microrobots and Teleoperations Workshop, 1987, 5 pages, IEEE.
Funda, Janez et al., "Constrained Cartesian Motion Control for Teleoperated Surgical Robots," IEEE Transactions on Robotics and Automation, IEEE, Jun. 1996, vol. 12, No. 3, pp. 453-465.
Furuta, Katsuhisa et al., "Master slave manipulator based on virtual internal model following control concept," IEEE Intl. Conference on Robotics and Automation, 1987, pp. 567-572, vol. 1, IEEE.
Goertz, Ray et al., "ANL mark E4A electric master slave manipulator," Proc 14th Conf. on Remote System Technology, 1966, pp. 115-123.
Green, Philip, S. et al., "Mobile telepresence surgery," 2nd Annual Intl Symposium on Med. Robotics and Computer Assisted Surgery, Maryland Nov. 1995, pp. 97-103.
Hannaford, Blake et al., "Computerized endoscopic surgical grasper," Proceedings, Medicine Meets Virtual Reality, San Diego, CA., 1998, 7 pages, IOS Press.
Hannaford, Blake et al., "Experimental and simulation studies of hard contact in force reflecting teleoperation," IEEE International Conference on Robotics and Automation Proceedings, 1988, pp. 584-589, vol. 1, IEEE.
Hill, John W., "Telepresence surgery demonstration system," Robotics and Automation, 1994, pp. 2302-2307, vol. 3, SRI International.
Howe, Robert D. et al., "Robotics for Surgery," Annu. Rev. Biomed. Eng, 1999, pp. 211-242, vol. 1.

(56) References Cited

OTHER PUBLICATIONS

Hurteau et al., "Laparoscopic surgery assisted by a robotic cameraman: Concept and Experimental results," IEEE International Conference on Robotics and Automation, May 8-13, 1994, pp. 2286-2289, vol. 3, IEEE.
Inoue, Masao; "Six-Axis bilateral control of an articulated slave manipulator using a Cartesian master manipulator," Advanced robotics, 1990, pp. 139-150, vol. 4—Issue 2, Robotic society of Japan.
International Search Report for application No. PCT/US02/38787, Mailed on Apr. 8, 2004, 1 page.
International Search Report for application No. PCT/US02/38790, Mailed on May 20, 2003, 1 page.
Jackson, Bernie G. et al., "Force Feedback and Medical Simulation," Interactive Technology and the New Paradigm for Healthcare, Morgan et al. (Eds ), 1995, pp. 147-151, vol. 24, IOS Press and Ohms.
Jones, Daniel B. et al., "Next generation 3D videosystems may improve laprascopic task performance," Interactive Technology and the New Paradigm for Healthcare, 1995, pp. 152-160, Ch 25.
Kazerooni, H., "Design and analysis of the statically balanced direct-drive robot manipulator," Robotics and Computer-Integrated Manufacturing, 1989, pp. 287-293, vol. 6, Issue 4.
Kazerooni, H. et al., "The Dynamics and Control of a Haptic Interface Device," IEEE Transactions on Robotics and Automation, 1994, pp. 453-464, vol. 10—Issue 4, IEEE.
Kazerooni, H., "Human/Robot Interaction via the Transfer of Power and Information Signals Part I: Dynamics and Control Analysis," IEEE International Conference on Robotics and Automation, 1989, pp. 1632-1640, IEEE.
Kim, Won S. et al., "Active compliance and damping in telemanipulator control," Jet Propulsion Laboratory New technology Report, 1991, pp. 1-14a, vol. 15—Issue 4, JPL & NASA Case No. NPO-1796917466, Item 40.
Kim, Won S. et al., "Remote Robot Control with High Force Feedback Gain," Technical Support Package NASA Tech Brief JPL New Technology Report NPO 18668, Aug. 1993, vol. 17—Issue 8, 44 pages.
Komatsu, Tadashi et al., "Control of a space flexible master slave manipulator based on parallel compliance models," IEEE International Conference on Robotics and Automation, 1998, pp. 1932-1937, vol. 3, IEEE.
Kwoh, Yik, San et al., "A Robot With Improved Absolute Positioning Accuracy for CT Guided Stereotactic Brain Surgery," IEEE Transactions on Biomedical Engineering, Feb. 1988, pp. 153-160, vol. 35—Issue 2, IEEE.
Lai, Fuji et al., "Evaluating control modes for constrained robotic surgery," IEEE International Conferenceon on Robotics & Automation San Francisco, Apr. 2000, vol. 1, pp. 603-609, IEEE.
Lorenz, Robert D. et al., "A Direct Drive Robot Parts and Tooling Gripper with High Performance Force Feedback Control," IEEE Transactions on Industry Applications, Mar./Apr. 1991, pp. 275-281, vol. 27—Issue 2, IEEE.
Mack, Michael J. et al., "Minimally Invasive and Robotic Surgery," JAMA, 2001, pp. 568-572, vol. 285—Issue 5.
Massie, Thomas H. et al., "The PHANTOM Haptic Interface: A Device for Probing Virtual Objects," Proceedings of the ASME Winter Annual Meeting, Symposium on Haptic Interfaces for Virtual Environment and Teleoperator Systems, 1994, 7 pages.
Mitsuishi, Mamoru et al., "A tele-micro-surgery system with co-located view and operation points and a rotational-force-feedback-free master manipulator," 2nd Annual Intl. Symposium on Medical robotics and Computer Assisted Surgery Baltimore Maryland, Nov. 4-7, 1995, pp. 111-118.
Neisius B. et al., "Robotic manipulator for endoscopic handling of surgical effectors and cameras," 1st Intl. Symposium on Medical Robotics and Computer Assisted Surgery, 1994, pp. 169-176, vol. 2.

Ng, W.S. et al., "Robotic Surgery, A First-Hand Experience in Transurethral Resection of the Prostate," IEEE Engineering in Medicine and Biology, Mar. 1993, pp. 120-125, vol. 12—Issue 1, IEEE.
Noonan, David, "The Ultimate Remote Control," Newsweek, Jun. 25, 2001, 7 pages total.
Parsell, D.L., "Surgeons in U.S. perform operation in France via robot," National Geographic News, Sep. 19, 2001, pp. 1-5.
Rosen, Jacob, et al., "Force controlled and teleoperated endoscope grasper for minimally invasive surgery," IEEE Experimental Performance Evaluation, IEEE, 1999, vol. 46, Issue 10, pp. 1212-1221.
Rotnes, Jan Sigurd et al., "Digital trainer developed for robotic assisted cardiac surgery," Studies in health technology and informatics, 2001, vol. 81, pp. 424-430.
Sabatini, A. M. et al., "Force Feedback Based Telemicromanipulation for Robot Surgery on Soft Tissue," IEEE Engineering in Medicine and Biology Society 11th Annual International Conference, 1989, pp. 890-891, vol. 3, IEEE.
Sastry, Shankar et al., "Millirobotics for remote minamally invasive surgery," Proceedings of the Intl. Workshop on Some Critical Issues in Robotics, Singapore, Oct. 2-3, 1995, pp. 81-98.
Sastry, Shankar, "MilliRobotics in Minimally Invasive Telesurgery," Internet, http://robotics.eecs.berkeley.edu, 1996, 8 pages.
Satava, Richard M., "Emerging technologies for surgery in the 21st century," Arch Surg, 1999, pp. 1197-1202, vol. 134.
Schaaf, Tracy A., "Robotic surgery: The future is now," Medical Device Link, Mar./Apr. 2001, pp. 1-13 Internet http://www.devicelink.com/mx/archive/01/03/0103mx024.html.
Schenker, Paul S. et al., "Development of a Telemanipulator for Dexterity Enhanced Microsurgery," 2nd Annual International Symposium on Medical Robotics and Computer Assisted Surgery, Nov. 4-7, Baltimore, Maryland, 1995, pp. 81-88.
Sharpe, J.E.E., "Human factors in the use of covariant bilateral manipulators," Ch. 24 Robot Control Theory and Applications Warwick K. and Pugh A. (Eds.) Peter Peregrinus Ltd. on behalf of the Institution of Electrical Engineers, Dec. 1988, pp. 219-236.
Spain, Edward H., "Stereo Advantage for a Peg in Hole Task Using a Force Feedback Manipulator," SPIE Stereoscopic Displays and Applications, 1990, pp. 244-254, vol. 1256, IEEE.
Sukthankar, Sujat M. et al., "Force Feedback Issues in Minimally Invasive Surgery," Interactive Technology and the New Paradigm for Healthcare, 1995, pp. 375-379, vol. 56, IOS Press and Ohmsha.
Sukthankar, Sujat M. et al., "Towards force feedback in laparoscopic surgical tools," IEEE Human Interface Laboratory Dept. of Biomedical Engineering, Ohio, 1994, pp. 1041-1042, IEEE.
Taubes, Gary et al., "Surgery in Cyberspace," Discover magazine, Dec. 1994, vol. 15, issue 12, pp. 85-92.
Taylor, Russell H. et al., "A Telerobotic Assistant for Laparoscopic Surgery," IEEE Engineering in Medicine and Biology, May/Jun. 1995, pp. 279-288, vol. 14, Issue 3, IEEE.
Tendick Frank, et al., "Analysis of the Surgeon's Grasp for Telerobotic Surgical Manipulation," IEEE 11th Annual Int Conf on Engineering in Medicine and Biology, Jun. 1989, pp. 914-915, IEEE.
Thring, M.W., Robots and Telechirs: Manipulators with Memory; Remote Manipulators; Machine Limbs for the Handicapped, 1983, pp. 9-11, 108-131, 194-195, 235-279; Ellis Horwood Limited, Chapter 5,7,8,9.
Trevelyan, James P. et al., "Motion Control for a Sheep Shearing Robot," IEEE Robotics Research Conference, the 1st International Symposium, Carroll, NH, USA., 1983, pp. 175-190, in Robotics Research, MIT Press.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Vibet, C., "Properties of Master Slave Robots," Motor-con, 1987, pp. 309-316.

(56) References Cited

OTHER PUBLICATIONS

Yokokohji, Yasuyoshi et al., "Bilateral Control of Master-Slave Manipulators for Ideal Kinesthetic Coupling—Formulation and Experiment-," Robotics and Automation, Proc. of IEEE International Conference on Robotics and Automation, May 12-14, 1992, pp. 849-858, vol. 1, IEEE.

* cited by examiner

TOOL GRIP CALIBRATION FOR ROBOTIC SURGERY

BACKGROUND OF THE INVENTION

The present invention is generally related to medical, telesurgical, and/or telerobotic devices, systems, and methods. In an exemplary embodiment, the invention provides structures and methods that calibrate an end effector/telerobotic manipulator combination when a new surgical robotic tool is mounted on a manipulator arm.

Minimally invasive medical techniques are intended to reduce the amount of extraneous tissue that is damaged during diagnostic or surgical procedures, thereby reducing patient recovery time, discomfort, and deleterious side effects. While many of the surgeries performed each year in the US could potentially be performed in a minimally invasive manner, only a portion of current surgeries use these advantageous techniques due to limitations in minimally invasive surgical instruments and the additional surgical training involved in mastering them.

Minimally invasive telesurgical systems for use in surgery have been developed to increase a surgeon's dexterity and avoid some of the limitations on traditional minimally invasive techniques. In telesurgery, the surgeon uses some form of remote control (such as a servomechanism or the like) to manipulate surgical instrument movements, rather than directly holding and moving the instruments by hand. In telesurgery systems, the surgeon can be provided with an image of the surgical site at the surgical workstation. While viewing a two or three dimensional image of the surgical site on a display, the surgeon performs the surgical procedures on the patient by manipulating master control devices, which in turn control the motion of servomechanically operated instruments. The servomechanism used for telesurgery will often accept input from two master controllers (one for each of the surgeon's hands) and may include two or more robotic arms or manipulators. Mapping of the hand movements to the image displayed from the image capture device can help the surgeon provide more direct control over movement of the surgical instruments.

While the new telesurgical systems and devices have proven highly effective and advantageous, still further improvements would be desirable. For example, work in connection with the present invention has shown that misalignment between a robotic surgical end effector and an input device can decrease the useful life of some tools, and efforts to limit such misalignment can make tool and manipulator fabrication more difficult than may be ideal. As many surgical tools may be mounted on any particular manipulator during a single surgical procedure, and as tool changes will be performed while a procedure is under way, it is generally preferable to avoid and/or minimize any tool-swap related delays to the surgical procedure.

For the reasons outlined above, it would be advantageous to provide improved devices, systems, and methods for robotic surgery, telesurgery, and other telerobotic applications. It would be particularly beneficial if these improved technologies enhanced the precision and alignment of sophisticated robotic systems without significantly increasing complexity or costs, ideally allowing greater tool useful life and reliability.

BRIEF SUMMARY OF THE INVENTION

The present invention generally provides improved telerobotic, telesurgical, and surgical robotic devices, systems, and methods. The present invention may calibrate end effectors having jaws or the like formed with two separate end effector elements. The grip calibration will often be performed selectively, without calibrating some or all of the other degrees of freedom of an end effector/manipulator assembly. Selective calibration of grip actuation can be performed by bringing the jaw elements into engagement with each other, such as by clamping a microforceps closed, fully closing an electrosurgical scissor, closing the jaws of a needle grasper (with no needle or other structure disposed between the grasper elements), and the like. Robotic systems employing commanded torque signals may be calibrated by bringing the end effector elements into engagement while monitoring the resulting position of a drive system, optionally identifying a maxima or minima of a second derivative of the torque data so as to identify an end effector engagement position. Calibration may be effected so that the end effector engagement position corresponds to a nominal closed position of an input handle. Such calibration can compensate for wear on the end effector, the end effector drive system, then manipulator, the manipulator drive system, the manipulator/end effector interfacing, and manufacturing tolerances of each of the components of the end effector/manipulator assembly.

In a first aspect, the invention provides a telesurgical system comprising an input handle having a first grip member that moves relative to a second grip member in response to a hand gripping the handle. A plurality of end effectors each have surgical jaws with a first end effector element moveable relative to a second end effector element. A manipulator transmits a signal in response to mounting an end effector on that manipulator. The mounted end effector may be one of the plurality of end effectors. A processor couples the input device to the manipulator, and is configured to calibrate the mounted end effector and manipulator in response to the signal. The processor does this by causing a calibration movement of at least one of the end effector elements so as to bring the elements into mutual engagement. The processor is configured to effect articulation of the jaws of the mounted end effector in response to the gripping of the handle per the calibration.

Typically, an input linkage supports the handle and a robotic arm of the manipulator supports the mounted end effector. The input linkage and robotic arm may each have a plurality of degrees of freedom. The processor may effect movement of the robotic arm in response to articulation of the input linkage. The processor may be configured to effect the calibration in response to mounting of the end effector onto the robotic arm before the end effector is used in a robotic surgical procedure. The processor may not determine calibration from a calibration movement of at least one degree of freedom of the robotic arm between mounting of the end effector and the robotic procedure, so that the processor selectively calibrates articulation of the jaws. Work in connection with the present invention indicates that end effector jaw alignment may limit robotic surgical tool life, may impose stringent manufacturing tolerances, and/or may impose drive system strength criteria which are more onerous than those needed for some or all other degrees of freedom in robotic surgical tools. Hence, by selectively calibrating end effector jaw engagement, overall surgical tool life, tolerances, and/or costs can be improved. In fact, the processor may not effect a calibration movement of any degree of freedom of the robotic arm between mounting of the mounted end effector and the robotic procedure, other than articulation of the jaws. While other degrees of freedom may benefit from calibration movements along with (or instead of) end effector jaw articulator, additional calibration movements of other degrees of freedom may undesirably delay resumption of a surgical procedure interrupted by a tool swap.

Typically, the calibration will compensate for manipulator offset, manipulator wear, manipulator manufacturing tolerances, surgical instrument offset, surgical instrument wear, surgical instrument manufacturing tolerances, manipulator/surgical tool interfacing, and/or the like. The processor may monitor movement of a drive system coupled to the end effector, and can identify a change in torque. The processor may optionally comprise a filter, and the processor may determine the change in torque by applying the filter to torque data. In the exemplary embodiment, the processor determines an end effector element initial engagement position by taking a second derivative of the torque data. As a servo control loop may calculate the commanded torque from a commanded trajectory and manipulator position data, the processor may command a trajectory and monitoring the commanded torque from the servo controller so as to determine a position of the end effector where the commanded torque changes.

The input device may apply a feedback force to the hand at a nominal closed position of the handle. The processor may affect the calibration so that the end effector initial engagement configuration corresponds to the nominal closed position of the handle. The handle may comprise a biasing means for increasing resistance to gripping of the handle beginning at the nominal closed position. The biasing means may comprise a spring, resilient bumper, or the like.

In some embodiments, a single-element end effector may also be couplable to the manipulator. A single-element end effector identifying signal may be transmitted by the manipulator when the single-element end effector is mounted thereon, and the processor may forego grip calibration in response to the single-element end effector signal. In an exemplary embodiment, a tool type identifier may be transmitted from a memory of a tool to the processor when a tool having the single-element end effector is mounted to the manipulator, the tool type identifier being used by the processor to look up, from a table of the processor's memory, a parameter indicating that grip calibration need not be performed.

In the exemplary embodiment, the processor is configured to effect the calibration once per robotic procedure for each end effector mounted on the manipulator. If an end effector is mounted on a second manipulator, the processor can again effect the calibration once per robotic surgical procedure for that end effector/manipulator combination. The calibration may be stored during the procedure in a memory of the processor so that when a tool has been removed from a particular manipulator and is subsequently remounted onto that manipulator, the calibration information can be applied without causing the calibration movement and the like.

In another aspect, the invention provides a telerobotic system comprising an input having a linkage supporting a handle. The handle has a first grip member that moves relative to a second group member when a hand grips the handle. The linkage is articulable for repositioning of the handle. A plurality of end effectors each comprise articulatable jaws with a first end effector element moveable relative to a second end effector element. A manipulator having a robotic arm movably supports a mounted end effector from among the plurality of end effectors. A processor couples the input device to the manipulator. The processor determines the calibration of the mounted end effector by causing a calibration movement of the end effector elements into mutual engagement. The processor effects articulation of the jaws of the mounted end effector in response to the gripping of the handle per the calibration.

In another aspect, the invention provides a telesurgical method comprising mounting a first surgical end effector to a manipulator. The end effector comprises jaws with a first end effector element movable relative to a second end effector element. The mounted first end effector and its supporting manipulator are calibrated by moving at least one of the end effector elements so as to bring the elements into mutual engagement. A handle is gripped with a hand so that a first grip member moves relative to a second grip member. An articulation signal is computed in response to the gripping of the handle per the calibration. The jaws articulate in response to the articulation signal so that the jaws of the first end effector move in correlation with the gripping of the handle.

DETAILED DESCRIPTION OF THE INVENTION

The present invention generally provides telerobotic, telesurgical, and surgical systems, devices, and methods. The invention is particularly advantageous for use with robotic surgical systems, in which a plurality of surgical instruments will be sequentially mounted on a manipulator during the surgical procedure. Loss of correlation between an input handle grip actuation and jaw articulation of telesurgical systems can be particularly problematic during telesurgery, and may be significantly more problematic than maintaining correlation between other input and output degrees of freedom in a surgical master/slave system. In some embodiments, by selectively calibrating end effector jaw movement (as opposed to calibrating all degrees of freedom of the slave), unnecessary surgical delays during tool swaps (in which one surgical instrument is removed from the manipulator and replaced with a different surgical instrument) can be avoided. In other embodiments, calibration of all axes may be performed.

While the most immediate applications for the present invention may include telesurgical systems, the inventions described herein may also find applications in other telerobotic and robotic surgical systems.

As used herein, the term "tool" encompasses robotic tools having robotic end effectors for coupling to robotic systems. The term "instrument" encompasses medical instruments, including both those having articulatable jaws (such as microforceps, needle graspers, staplers, electrosurgical scissors, and the like) and those having a single end effector element (such as scalpels, electrosurgical coagulators, and the like). In the exemplary embodiment, a robotic surgical system makes use of a series of removable and replaceable end effectors supported by a robotic arm, so that the end effector assembly is both a tool and an instrument. In robotic embodiments used in non-surgical applications, the end effector assembly may comprise a robotic tool that is not a medical instrument.

The data, reprogrammable software, program method steps, and method steps described herein may be embodied in a machine readable code and stored as a tangible medium in a wide variety of differing configurations, including random access memory, non-volatile memory, write once memory, magnetic recording media, optical recording media, and the like. Along with software, at least some of the programming and data may be embodied in the form of hardware or firmware.

Figure 1:
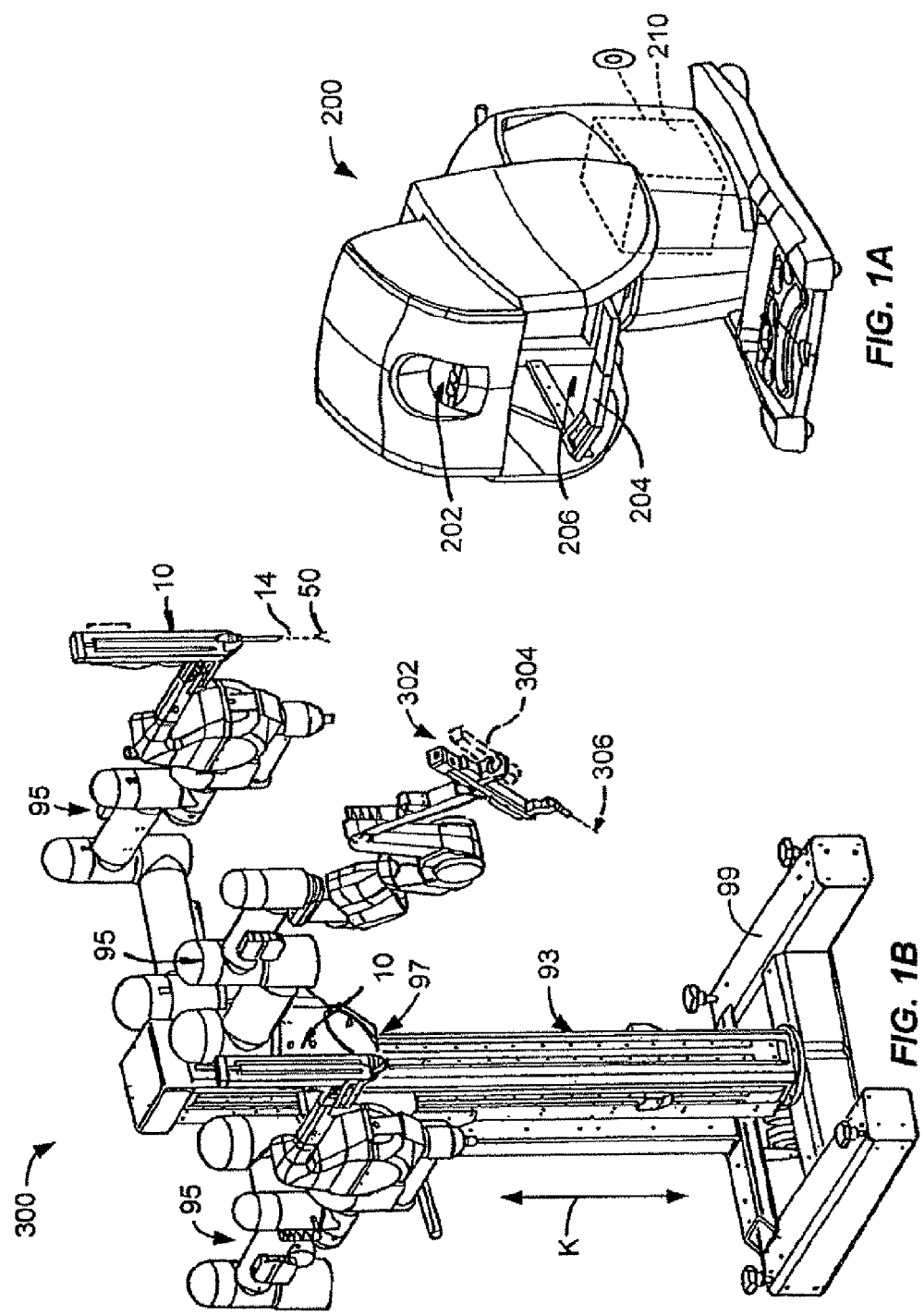
FIGS. 1A and 1B are perspective views illustrating a master surgeon console or workstation for inputting a surgical procedure, and a robotic patient-side cart for robotically moving surgical instruments having surgical end effectors at a surgical site, respectively.

Referring to FIG. 1A of the drawings, an operator workstation or surgeon's console of a minimally invasive telesurgical system is generally indicated by reference numeral 200. The workstation 200 includes a viewer 202 where an image of a surgical site is displayed in use. A support tool 4 is provided on which an operator, typically a surgeon, can rest his or her forearms while gripping two master controls (see FIG. 2), one in each hand. The master controls or input devices are positioned in a space 206 inwardly beyond the support 204. When using the control workstation 200, the surgeon typically sits in a chair in front of the control station, positions his or her eyes in front of the viewer 202 and grips the master controls, one in each hand, while resting his or her forearms on the support 204.

In FIG. 1B of the drawings, a cart or surgical station of the telesurgical system is generally indicated by reference numeral 300. In use, the cart 300 is positioned close to a patient for whom surgery is planned, and the base of the cart is then maintained at a stationary position until a surgical procedure has been completed. Cart 300 typically has wheels or castors to render it mobile. The workstation 200 is typically positioned at some distance from the cart 300, optionally being separated by a few feet within an operating room, although cart 300 and workstation 200 may alternatively be separated by a significant distance.

The cart 300 typically caries three robotic arm assemblies, although more than three arms may also be provided or may be the norm for some embodiments. One of the robotic arm assemblies, indicated by reference numeral 302, is arranged to hold an image capturing device 304, e.g., an endoscope, or the like. Each of the two other arm assemblies 10 includes a surgical instrument 14. The endoscope 304 has a viewing end 306 at a distal end of an elongate shaft. Endoscope 304 has an elongate shaft to permit viewing end 306 to be inserted through an entry port into an internal surgical site of a patient's body. The endoscope 304 is operatively connected to the viewer 202 to display an image captured at its viewing end 306 on the viewer. Each robotic arm assembly 10 is normally operatively connected to one of the master controls, although the processor may alter which robotic arm assembly is operatively connected with a master control. Thus, the movement of the robotic arm assemblies 10 is controlled by manipulation of the master controls. The instruments 14 of the robotic arm assemblies 10 have end effectors mounted on wrist members, which are in turn pivotally mounted on distal ends of elongate shafts of the instruments 14. Instruments 14 have elongate shafts to permit the end effectors to also be inserted through entry ports into the internal surgical site of a patient's body. Movement of the end effectors relative to the ends of the shafts of the instruments 14 is also controlled by the master controls.

The robotic arms 10, 302 are mounted on a carriage 97 by means of setup joint linkages 95. The carriage 97 can be adjusted selectively to vary its height relative to a base 99 of the cart 300, as indicated by arrows K. The setup joint linkages 95 are arranged to enable the lateral positions and orientations of the arms 10, 302 to be varied relative to a vertically extending column 93 of cart 300. Accordingly, the positions, orientations and heights of the arms 10, 302 can be adjusted to facilitate passing the elongate shafts of the instruments 14 and the endoscope 304 through the entry ports to desired positions relative to the surgical site. When the surgical instruments 14 and endoscope 304 are so positioned, the setup joint arms 95 and carriage 97 are typically locked in position. Workstation 200 and cart 300 are described in more detail in U.S. Pat. No. 6,424,885, the full disclosure of which is incorporated herein by reference.

Figure 2:
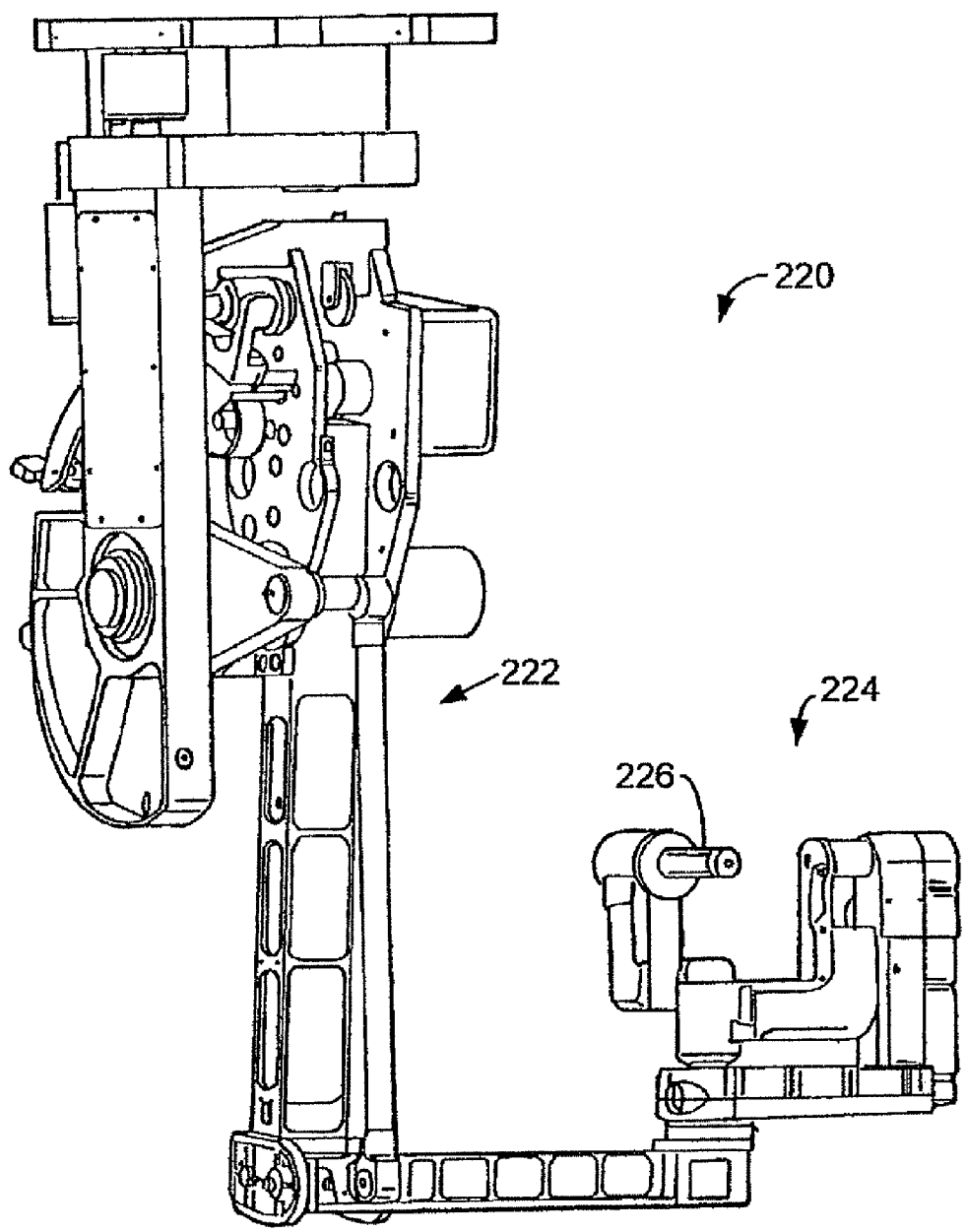
FIG. 2 is a side view showing an exemplary input device for use with the master control workstation of FIG. 1A.
Figure 3:
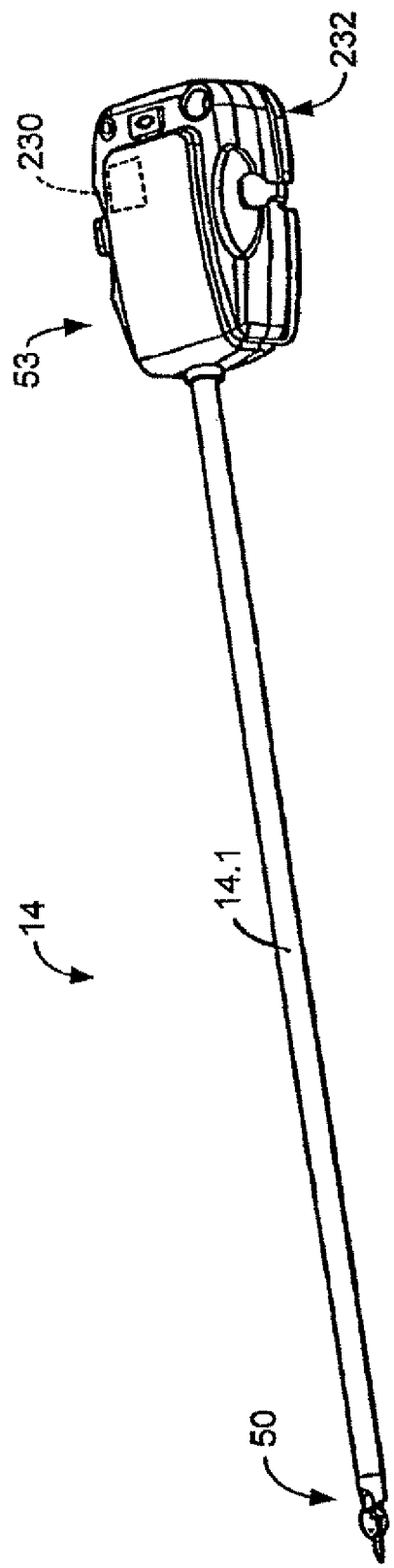
FIG. 3 is a perspective view of an exemplary robotic surgical instrument or tool having a memory and a data interface.
Figure 3A:
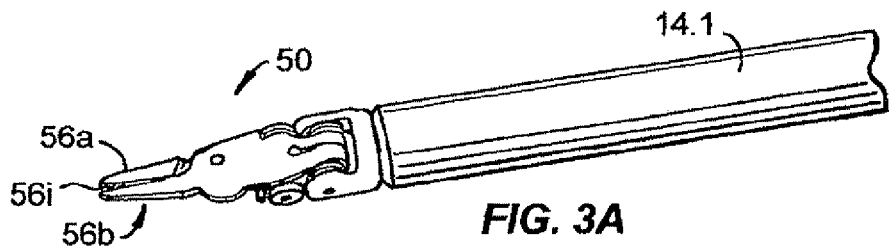
FIGS. 3A-3F are perspective views of a plurality of different end effectors for surgical instruments of different types.
Figure 3B:
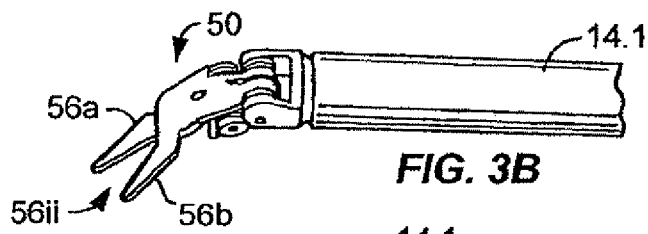
Figure 3C:
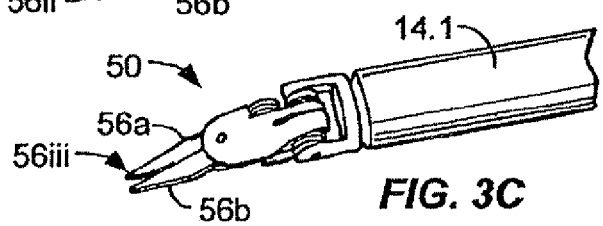

An exemplary input device 220 and surgical instrument 14 are illustrated in FIGS. 2 and 3, respectively. Input device 220 includes an arm 222 and a wrist 224 which allow positional and orientational movement of an input handle 226 relative to the structure of workstation 200 (see FIG. 1A). Handle 226 will generally move with a plurality of degrees of freedom relative to the workstation structure, the exemplary input device 220 providing six degrees of freedom for movement of handle 226. The linkage supporting the handle may include more or less than six degrees of freedom.

Figure 2A:
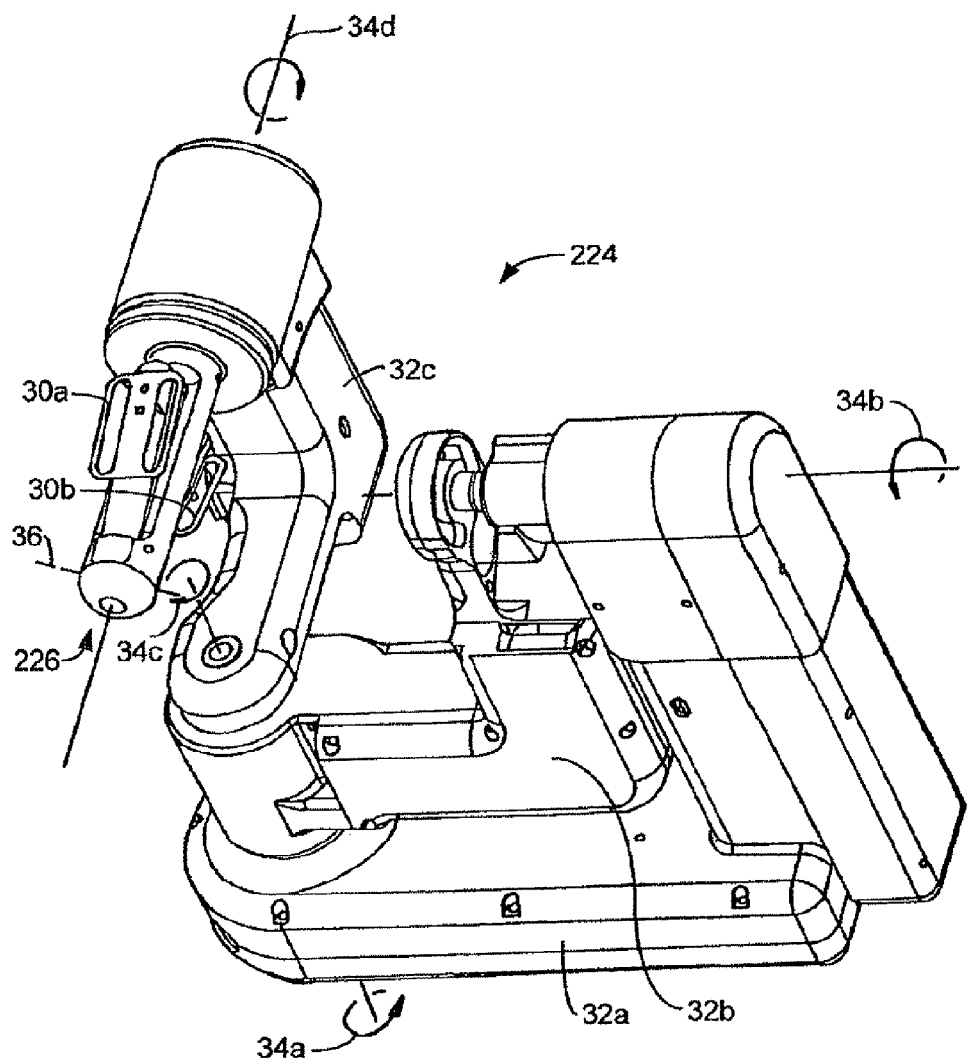
FIG. 2A is a perspective view of a handle and wrist of the input device of FIG. 2.

FIG. 2A illustrates wrist 224 and handle 226 in more detail. Wrist 224 generally comprises a gimbal assembly supporting handle 226, with the handle having first and second grip members 30a, 30b. Wrist 224 generally accommodates changes in orientation of handle 226 with three orientational degrees of freedom.

In the exemplary embodiment, wrist 224 includes links 32a, 32b, and 32c. Wrist 224 is mounted to input arm or linkage 222 (see FIG. 2). The links of the wrist can rotate about axes 34a, 34b, 34c, and 34d. Hence, wrist 224 provides four orientational degrees of freedom, including one redundant orientational degree of freedom. A drive system is coupled to the wrist links so as to take advantage of this redundant degree of freedom and provide a wide range of motion as described in U.S. Pat. No. 6,714,839 entitled "Master Having Redundant Degrees of Freedom", the full disclosure of which is incorporated herein by reference.

Unlike the joints of wrist 224 and input linkage 222, grip members 30a and 30b of handle 226 pivot passively about an axis 36 with no drive motor provided for feedback from the slave. In the exemplary embodiment, a hall effect transducer is mounted in one of the grip members and a magnet is mounted in the other, so that handle 30 generates a grip signal indicating the angular separation between grip numbers 30a and 30b. A biasing system urges the grip members apart, and the grip members may include loops of Velcro™ or the like to more firmly position the grip members relative to a thumb and finger of the system operator. A wide variety of grip member structures might be used within the scope of the invention, including any surgical instrument handles, optionally including rigid or flexible loops for the thumb and/or fingers.

Referring now to FIG. 3, surgical instrument 14 generally includes a surgical end effector 50 supported relative to a housing 53 by an elongate shaft 14.1. End effector 50 may be supported relative to the shaft by a distal joint or wrist so as to facilitate orienting the end effector within an internal surgical workspace. Proximal housing 53 will typically be adapted to be supported by a holder of a robot arm.

As described in more detail in U.S. Pat. No. 6,331,181, the full disclosure of which is incorporated herein by reference, instrument 14 will often include a memory 230, with the memory typically being electrically coupled to a data interface of a holder engaging surface 232 of housing 53. This allows data communication between memory 230 and a robotic surgical processor 210 of workstation 200 (see FIG. 1A). In th exemplary embodiment, memory 230 comprises a Dallas chip sold with part number DS2505 having 69 kilobits of data storage capacity.

Referring now to FIGS. 3A-3F, a variety of alternative robotic surgical tools of differing types and having differing end effectors 50 may be provided. Several of these end effectors, including DeBakey forceps 56i, microforceps 56ii, Potts scissors 56iii, and clip plier 56iv include first and second end effector elements 56a, 56b which pivot relative to each other so as to define a pair of end effector jaws. Other end effectors, including scalpel 56v and electrocautery probe 56vi have a single end effector element.

While the present invention may find applications with surgical robotic end effectors having a single element, the invention is particularly advantageous for use with end effectors defined by multiple end effector elements. In many embodiments, the tool or end effector type can be recognized by the system through reading of some or all of the data stored by memory 230 mounted on tool 14 (see FIG. 3).

Information from the memory can be used to perform a number of functions when the tool is loaded on the tool holder of the manipulator arm. For example, the memory can be used to provide a signal verifying that the tool is compatible with the robotic system. The tool memory may store data identifying the tool type to the robotic system so that the robotic system can reconfigure its programming to take full advantage of the tool's specialized capabilities. The tool memory can also store a specific or unique identifier for that particular tool for use in controlling tool life and hence reliability, for determining whether calibration of that particular tool has already been performed during the current (or in some embodiments, a prior) procedure, and the like. Exemplary surgical robotic tool/manipulator interface structures and details regarding data transfer between tools and robotic system processors are more fully described in U.S. Pat. No. 6,331,181 and in an application entitled, "Tool Memory Based Software Upgrades for Robotic Surgery", filed concurrently herewith.

Figure 3D:
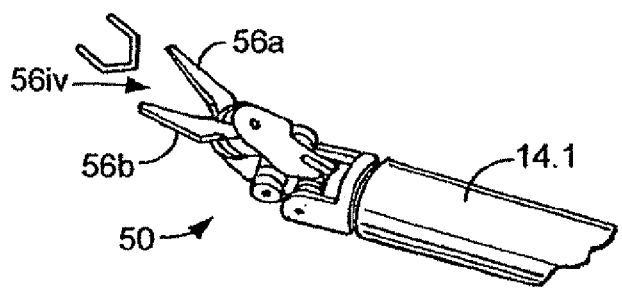
Figure 3E:
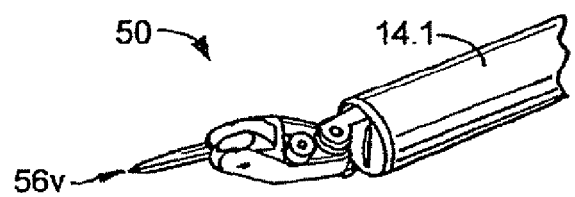
Figure 3F:
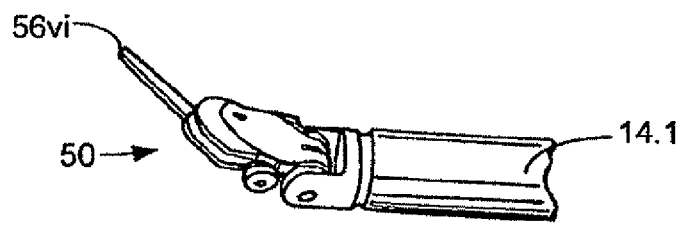
Figure 4:
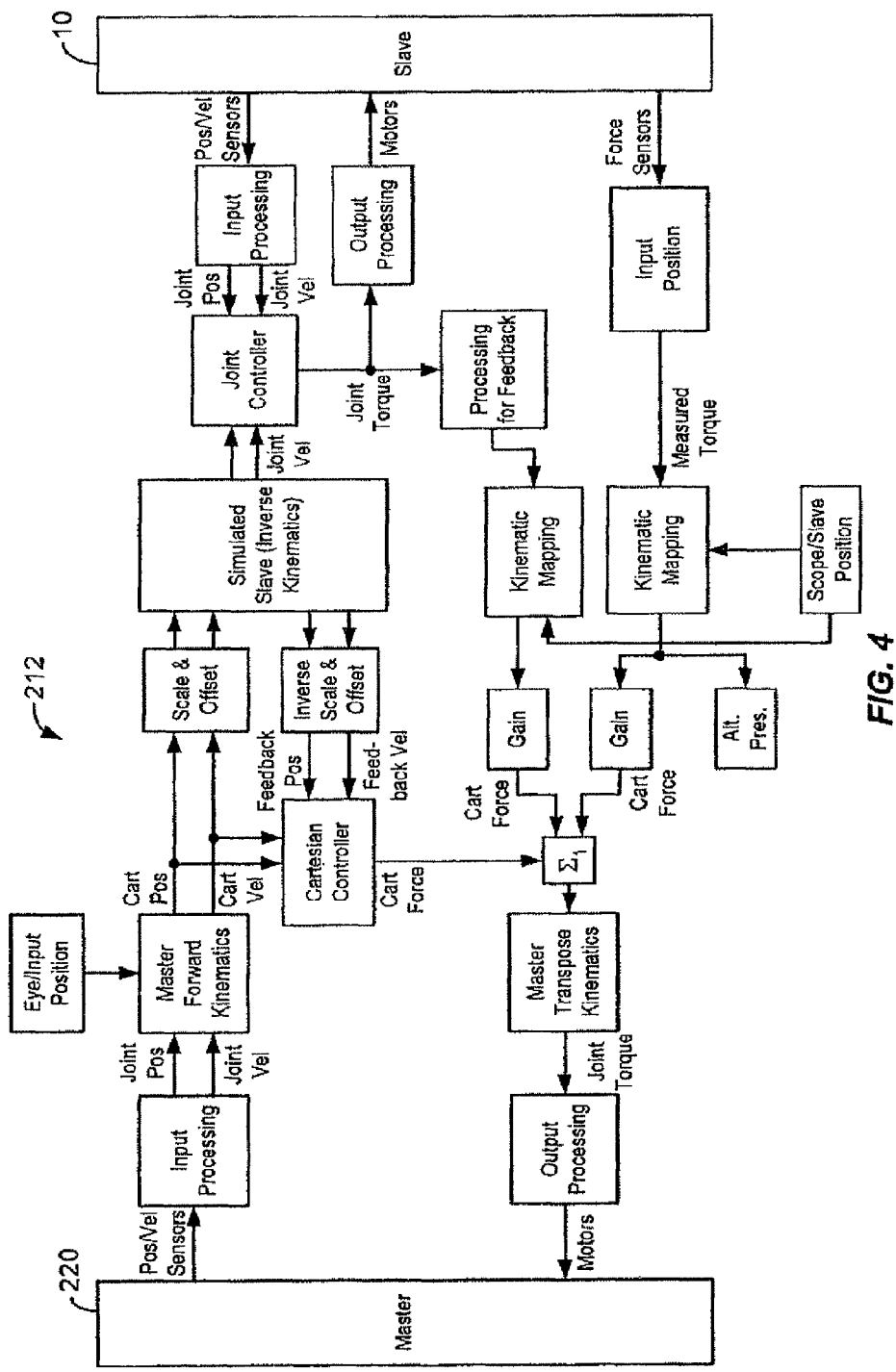
FIG. 4 shows a block diagram representing control steps followed by the control system of a minimally invasive surgical robotic apparatus in effecting movement of the end effector of the instrument of FIG. 3 in response to the movement of the input device of FIG. 2.

As can be understood by reference to FIGS. 1A, 1B, and 4, processor 210 of workstation 200 may be configured to effect corresponding movement of a surgical instrument mounted to a robotic arm in response to movement of an input handle by employing software embodying a control logic 212. Control logic 212 effects movement of end effector 50 within an internal surgical site by pivoting an instrument shaft 14.1 about a minimally invasive insertion point (see FIG. 3). The control logic 212 employed by processor 210 generates motor drive signals in response to an input handle movement. These motor drive signals are transmitted to the robot arms, and cause movement at the end effector that corresponds to movement at the input handle. Logic 212 of processor 210 can accommodate a wide variety of differing tool kinematics of a variety of differing tools (such as those illustrated in FIGS. 3A-3F) when information regarding the tool type currently mounted to a robotic arm is made available to the processor.

Maintaining precise control over movement of surgical tools in general, and robotic surgical tools in particular, enhances the safety and therapeutic benefits of surgery. The use of elongate, relatively thin surgical instruments also enhances the benefits of robotic surgery, as such thin-shafted instruments can be inserted to an internal surgical site with less trauma to the patient. The surgical instruments, however, can be fairly sophisticated and complex mechanical assemblies, particularly where a plurality of end effector elements and/or degrees of freedom are provided at the distal end of the elongate shaft. Instruments 14 may include drive systems comprising cables, pulleys, rods, gears, and the like, and these mechanical components are subject to both manufacturing tolerances and wear during the life of the tool. Additionally, the manipulator or robotic arm on which the tool is mounted may have a drive system for both transmitting motion to the tool and for moving the tool holder in space, along with having motors and position sensors for receiving drive signals from and transmitting feedback signals to the processor of the robotic system. Many of these components are also subject to deterioration from wear, along with having an initial resolution or tolerance when new. Lastly, coupling of the instrument to the robotic arm via the holder will often comprise a mechanical engagement so as to transmit mechanical movement from the motor and drive system of the robotic arm to the end effector, along with structural engagement between the housing of the instrument and the holder itself. Hence, misalignment between the end effector and an input device may have a number of sources, and may vary significantly between different robotic arms and tools mounted on robotic arm combinations.

Telesurgical and other telerobotic systems can accommodate a certain amount of misalignment between an input device and an end effector, as described more fully in U.S.

Pat. No. 6,424,885, the full disclosure of which is incorporated herein by reference. However, misalignment between the gripping members of a handle and the end effector elements of a pair of jaws can be particularly problematic.

Figure 6A:
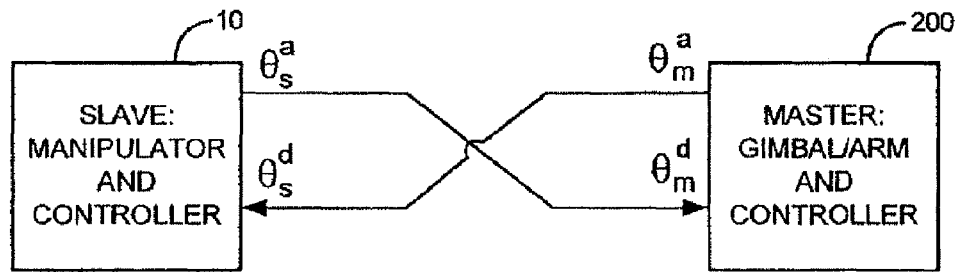
FIGS. 6A-6C are functional block diagrams schematically illustrating master/slave arrangements for manipulating the position, orientation, and jaws of a robotic surgical instrument.

Referring now to FIG. 6A, a simplified reciprocal master/slave arrangement is used to illustrate actuation of manipulator 10 so as to provide orientation and positioning of end effector 50 in response to movement of handle 226 of the input controller 200. It should be understood that the various master and slave positions θ may comprise vectors (in Cartesian space, polar space, joint space, or the like) as well as simple angles or linear separations, and the kinematic chains of the master and slave may be quite different, often even having different degrees of freedom. To provide force feedback to the operator, the master input device is actively driven by its motors toward alignment with the position occupied by slave 10. The amount of following force applied by the operator on the slave (and the reciprocal feedback on the operator's hand) are a function of a misalignment between a position (and orientation) of the master input device and apposition (and orientation) of the slave end effector.

As illustrated schematically in FIG. 6A, master input device 200 defines an actual master position $\theta_m^a$. This actual position of the master is fed into the slave portion of the controller as a desired slave position $\theta_s^d$. The amount of force applied by the end effectors of the slave will vary with the difference between the desired position of the slave $\theta_s^d$ and the actual position of the slave $\theta_m^a$, with the following force on the end effectors increasing with increasing misalignment between the actual and desired positions, often with a proportional relationship.

To provide force feedback to the operator manipulating the master input device 200, the actual slave position $\theta_m^a$ is fed back into the motors of the input device as a desired master position $\theta_s^d$. Once again, the amount of force imposed by the motors of the master on the operator through the input device will vary with the misalignment or positional separation between the desired master position and the actual master position. This allows the operator to apply varying amounts of force through the servomechanism using the end effectors, and to have tactile feedback regarding the amount of force that has been applied.

While the reciprocal master/slave arrangement of FIG. 6A may be implemented to actuate end effector 50 in response to manipulation of handle 226 for gripping of objects between end effector elements 56a and 56b, the uniform following forces provided by this arrangement can have disadvantages, as can be understood with reference to FIGS. 5A-5D. End effector 50 is first shown engaging a relatively large tissue T1 with no gripping force. The master position $\theta_m$ is equal to the slave position $\theta_s$. As there is no difference between the signals generated to measure these positions, the positional error signal, separation misalignment, and following forces are all zero.

Figure 5A:
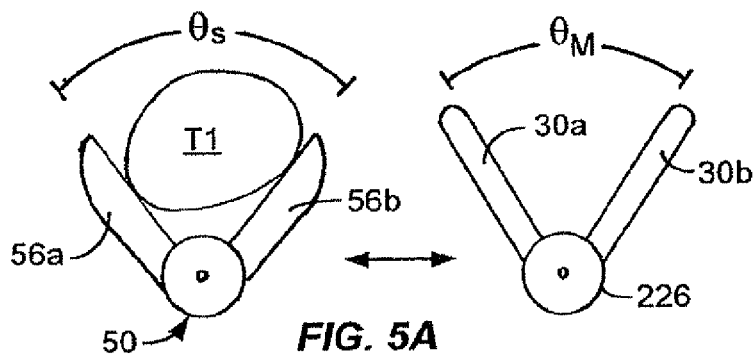
FIG. 5A-5D schematically illustrate master/slave following forces applied to grip different sized objects.
Figure 5B:
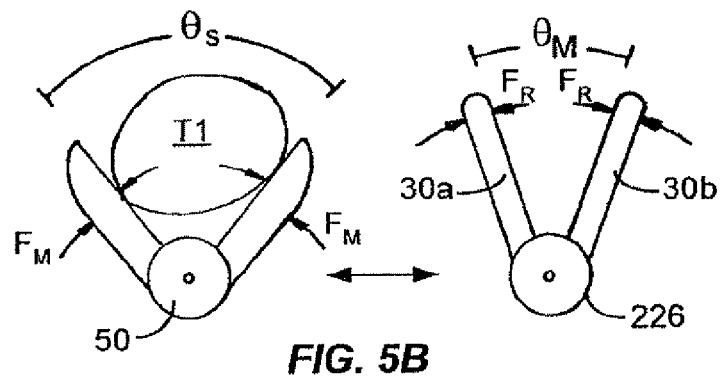

Referring now to FIG. 5B, as the operator imposes squeezing forces on handle 226 to bring gripping members 30a, 30b closer together (and thereby reducing the separation angle), the servomechanism begins to apply the following forces against end effector 50. As the difference between the grip angle and end effector angle increases, the following forces imposed by the end effector elements against the large tissue T1 (and the reactive forces of the tissue against the end effector) increase. Eventually, the following forces reach a maximum $F_m$, which may be determined by a strength of the surgical tool, a limitation of the motor torque, or a limitation based on the intended uses of the tool (for example, to avoid severing of tissues with forceps). Regardless, the servomechanism will preferably limit the following forces before irreparable damage is inflicted on the robotic system.

To implement maximum following forces $F_m$, the operator has squeezed gripping members 30a, 30b well beyond the separation angle between the end effector elements. While it is generally preferable to maintain a one-to-one correlation between the angles of the gripping members and end effector elements, having a significant misalignment to effect the maximum following forces is generally acceptable when the separation angle of the gripping members remains significantly above zero once the maximum following force $F_m$ is imposed. Optionally, handle 30 may impose reciprocal forces $F_r$ against the hand of the operator to provide a tactile indication of the strength with which thick tissue T1 is being gripped to the operator.

Figure 5C:
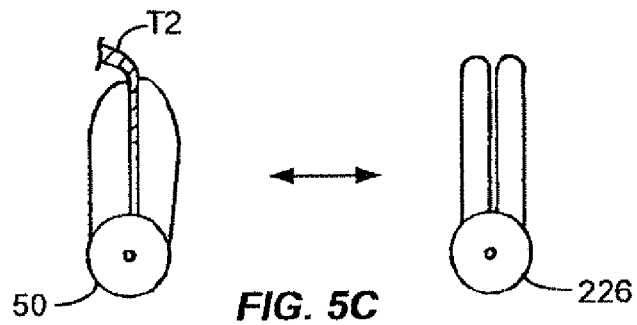
Figure 5D:
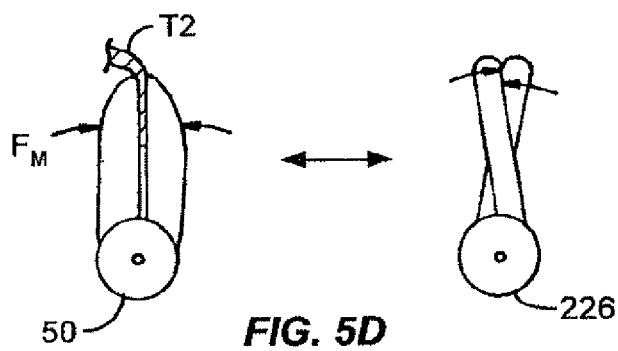

As illustrated in FIGS. 5C and 5D, the situation is less acceptable when a thin tissue T2 of negligible thickness is gripped. When just engaging the tissue with the elements of end effector 50, the gripping members of handle 226 again define a separation angle that is substantially equal to the separation angle defined by the end effector elements. However, as this gripping configuration provides a quite small angular separation between the gripping members, imposition of maximum following forces $F_m$ against small tissue T2 only results when the gripping members are pushed beyond each other to define a negative gripping angle. This unnatural gripping actuation detracts from the operator's ability to accurately control the end effectors, particularly during delicate telepresence procedures involving the gripping of small objects, such as sutures, needles, and small tissues during telesurgery.

Figure 6B:
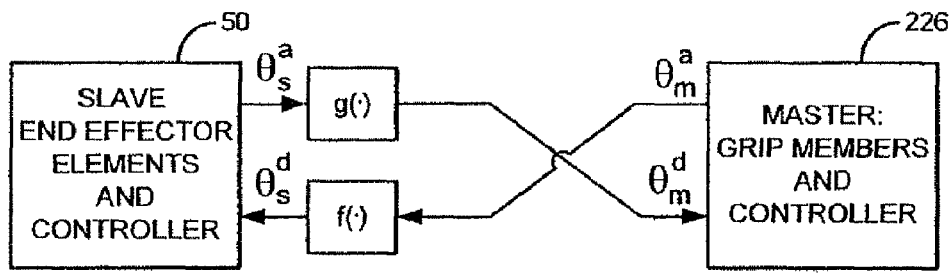

Referring now to FIG. 6B, an alternative servomechanism arrangement artificially alters the actual master position $\theta_m^a$, according to a function f to derive a desired slave position $\theta_s^d$. Function f takes the form $\theta_s^d = f(\theta_m^a)$, and is preferably an invertible (monotonic) and continuous function of the actual master position. Function g represents reciprocal forces imposed on the hand of the system operator, and will preferably also comprise a continuous, invertible function. Preferably g will provide one-to-one actuation when open, will have the slave just closed when the master is just closed, and will have a slope below the "just closed" point so that the restoring force applied against the operator's hand matches that of a conventional tool, thereby providing feedback to the operator accurately reflecting the enhanced forces provided when the end effector and handle are near their closed configurations.

As can be understood with reference to FIGS. 6B and 5D, function f may be tailored so that once the separation between the gripping members drops below a predetermined point a small additional decrease in gripping member separation $\theta_m^a$ will result in a significantly larger change in the desired position of the slave $\theta_s^d$. Above the predetermined point, the actual master position and desired slave position can remain the same, thereby providing the greatest dexterity for the system operator's control over the end effector.

Figure 6C:
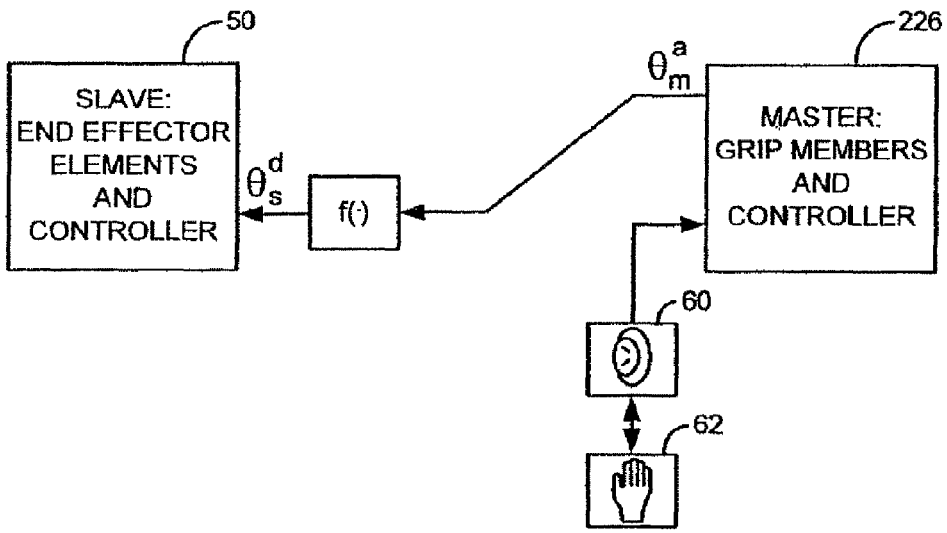

Referring now to FIG. 6C, an alternative servomechanism arrangement makes use of function f to alter the actual position of the grip members so as to generate the desired position of the slave end effector, as described above. However, rather than relying on a reciprocal master/slave arrangement to provide feedback of the augmented end effector forces as the grip members and end effector elements approach their closed configuration, the system of FIG. 5C relies on a biasing system 60 which interacts with the operator's hand 62 to provide tactile feedback to the operator with a feed forward system, as can be understood with reference to U.S. Pat. No. 6,594,552, the full disclosure of which is incorporated herein by reference.

Figure 7:
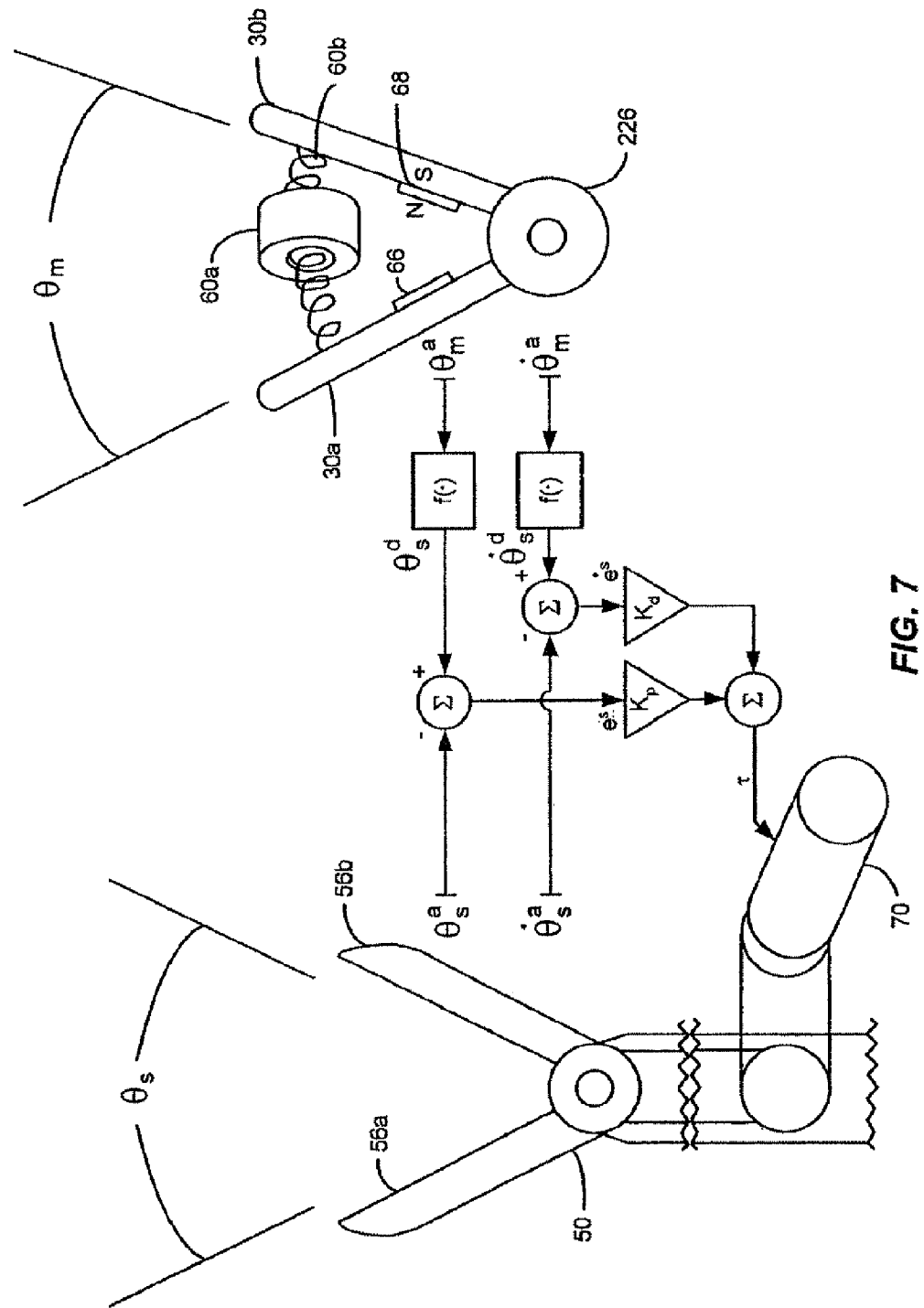
FIG. 7 schematically illustrates an exemplary master/slave robotic control system for actuating jaws of an end effector while providing tactile feedback to a hand of an operator.

As can be understood with reference to FIG. 7, a biasing mechanism such as a spring, magnet, resilient bumper, or the like can define a predetermined transition point or nominally closed position of the input handle. In the exemplary embodiment, a biasing system includes an elastomeric bushing 60a surrounding a grip return spring 60b. The grip return spring opens the gripping members of handle 226 throughout their range, while the bushing provides tactile feedback to a hand of an operator when the handle reaches a nominal closed position. Continued movement of the gripping members is possible beyond the nominal closed position so as to apply force at the end effector elements. Torques are applied to end effector elements 56a, 56b and positions of the end effector elements are measured via a drive system 70, as described more fully in the '555 patent.

Figure 8:
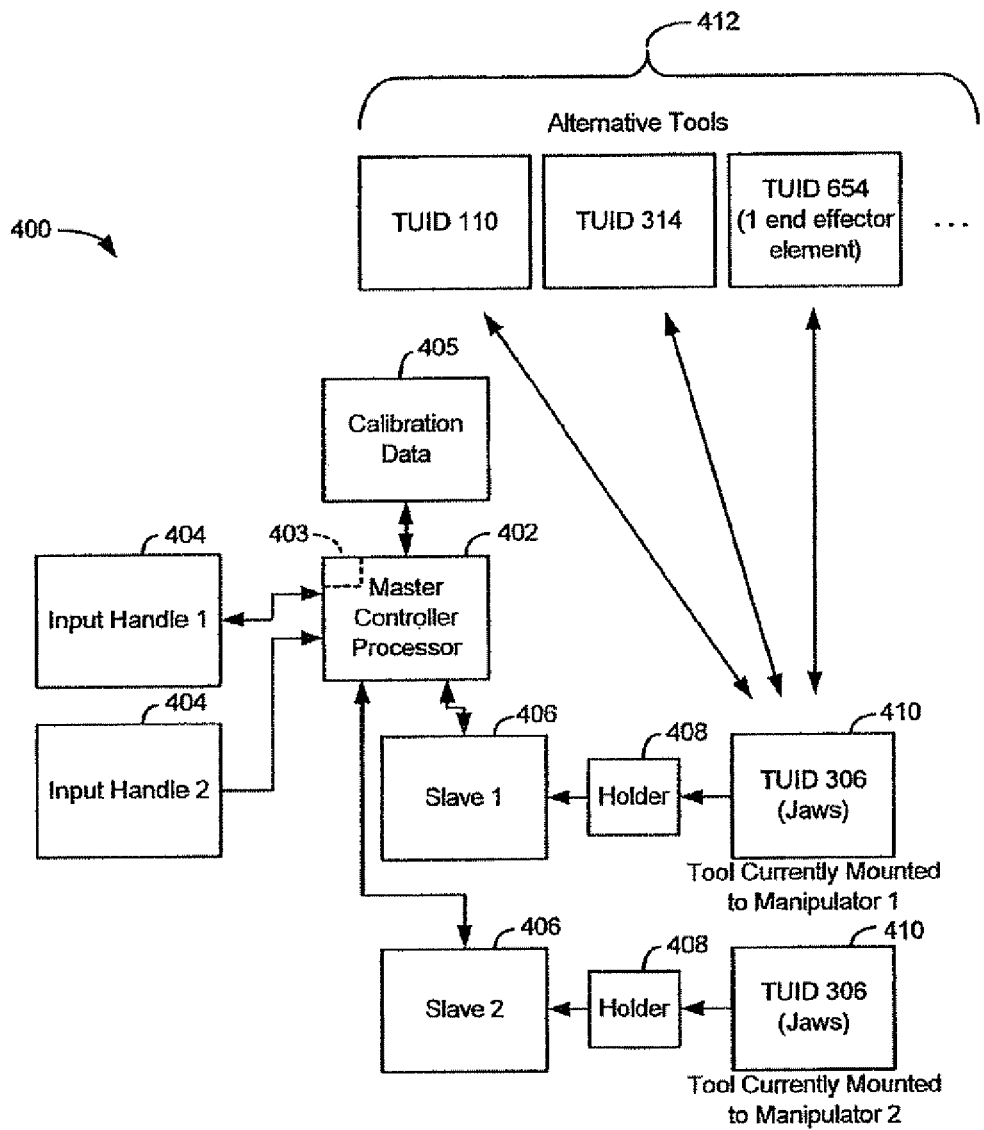
FIG. 8 is a functional block diagram schematically illustrating a telesurgical system according to the principles of the present invention.

Referring now to FIG. 8, a robotic surgical system 400 includes a processor 402 coupling first and second input devices 404 to associated robotic manipulators 406. Each manipulator includes a tool holder 408 that both holds and provides a data interface with a mounted tool 410. As tools will often be removed and replaced repeatedly during a surgical procedure, for example, to allow use of an electrocautery paddle followed by a needle grasper, a plurality of alternative tools 412 are available to be used in place of either of the mounted tools.

When one type of tool is removed from holder 408 and replaced by another type of tool, data from tool memory 230 (see FIG. 3) is transmitted from the newly mounted tool to the processor 402. This allows the processor to be reconfigured so as to allow the surgeon to accurately and safely use tools of different types. This data may also include a specific tool identifier so as to allow the processor to determine or monitor characteristics and use of that particular tool, including tool life, etc. As explained in more detail in an application entitled "Tool Memory-Based Software Upgrades for Robotic Surgery,", filed concurrently herewith and incorporated herein by reference, the tool memory may also be used to update data and/or software stored in a memory of processor 402, thereby allowing the use of new tools which have been developed, approved, and/or distributed a most recent software revision has been downloaded to processor 402 using conventional storage media, network connections, or the like. The grip calibration procedure described herein may take place at least in part during downloading of data from mounted tool 410 so as to avoid unnecessary delays in a procedure, and need not be implemented if processor 402 determines it is not needed, for example, if a tool type identifier stored in a memory of the tool and transmitted from the slave indicates that the mounted tool has only a single end effector or if the desired grip calibration data is already stored in a grip calibration table 405 in a memory of the processor.

For the present invention, processor 402 may determine whether a particular tool has been loaded on a specific manipulator, and may store grip calibration data for that tool/manipulator combination in grip calibration table 405. That grip calibration data may optionally be used if the same tool is remounted on the same manipulator. Such re-use of grip calibration data may be limited, so that the data will only be used if the tool is remounted within a time span, during a surgical procedure, a number or amount of tool use, or prior to some event.

Manipulator 406 often transmits a signal to processor 402 indicating that a tool has been mounted to holder 408.

Processor 402 includes a grip calibration module 403, which may include hardware, software, and/or a combination of both, the grip calibration module often comprising machine readable code embodying programming instructions for implementing a grip calibration method, optionally in response to the tool-mounting signal. Using this grip calibration method, processor 402 can determine and store an end effector/manipulator grip offset, which can include offsets of the instrument (due to cable stretch, manufacturing offsets, and the like), offsets of the manipulator 406 (including homing error, calibration, cable stretch, and the like), and/or interface offsets resulting from the combination of tool interface 232 (see FIG. 3) with holder 408. Hence, the grip calibration module of processor 402 can compensate for these offsets so as to improve following of end effector jaws in response to grasping of a handle 404. By adjusting processor 402 so as to compensate for aging of the manipulator and/or end effector, the grip calibration module may maintain or improve performance of used instruments.

Figure 9:
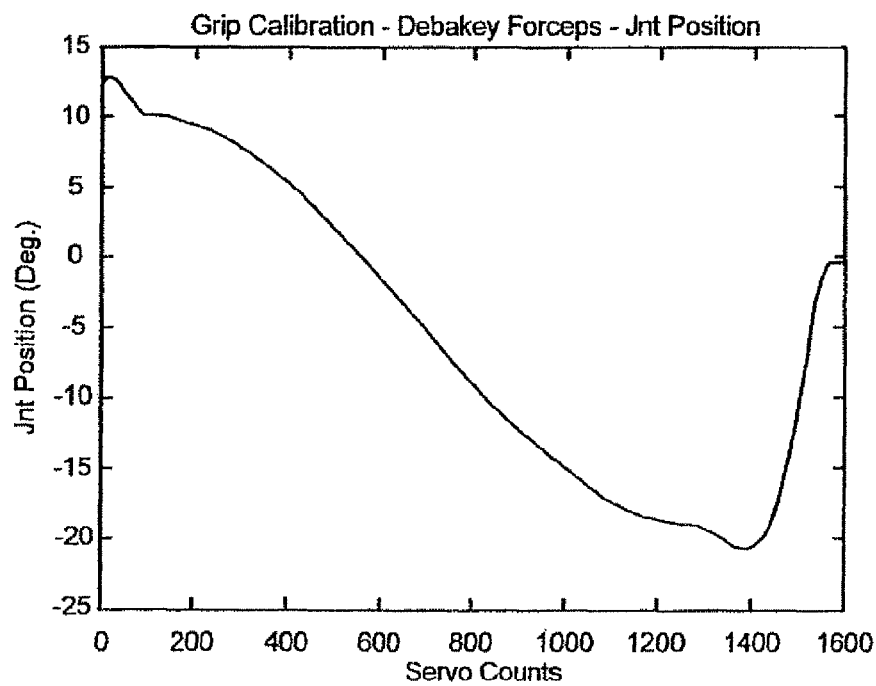
FIG. 9 graphically illustrates a relationship between joint position and servo counts during actuation of a surgical robotic end effector in the system of FIG. 8.
Figure 10:
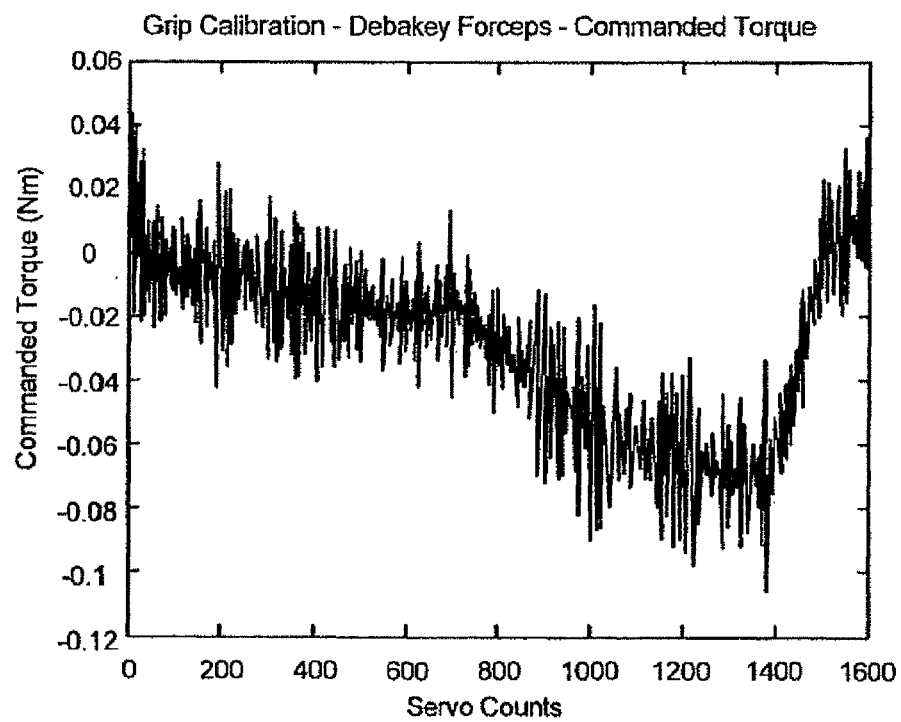
FIG. 10 graphically illustrates a relationship between commanded torque and servo counts during end effector actuation in the system of FIG. 8.

Referring now to FIGS. 8, 9, and 10, after instrument mounting, processor 402 implements the grip calibration method. A tool type identifier and a specific tool identifier may be transmitted by the manipulator from the memory of the tool to the processor, allowing the processor to determine whether grip calibration is appropriate. For example, the processor may look-up a parameter in a table of the processor memory associated with the tool type identifier, so that tools having single end-effector elements do not undergo a grip calibration, or so that a clip applier (as illustrated in FIG. 3D) does not deploy a clip during calibration. Alternatively, the processor may determine from the tool identifier that the mounted tool has previously been mounted to the same manipulator previously during the same procedure, and may therefore look-up the desired calibration information from a calibration data table 405. The calibration data table my comprise jaw closure offset for specific tool manipulator combinations.

If processor 402 determines that a new calibration procedure is appropriate for the mounted tool, the processor transmits drive signals to manipulator 408 on which a tool 410 has been mounted. In response to these signals, one or more motors of manipulator 406 move the end effectors into mutual engagement, with the motors typically applying torque to the end effectors via a coupling drive system (see FIG. 12) so as to attempt to move even further against each other, thereby squeezing the end effector closed. In the exemplary embodiment, the processor may command a trajectory or movement of the end effector, causing a servo controller loop of the processor to calculate a commanded motor torque using a position of the end effector element. Processor 402 monitors and stores joint position and commanded torque data as illustrated in FIGS. 9 and 10, respectively. The servo counts shown in FIGS. 9-12C can represent time, with the exemplary servo loop operating with a cycle frequency of 1333 Hz.

When the end effector elements are commanded to move from an open configuration to beyond a closed configuration, a significant change in commanded torque may be expected where the end effector are first fully closed, which may be referred to as a mutual engagement configuration. In other words, the associated motor will be driven harder to effect the commanded movement after the end effectors begin pushing against each other. This change in commanded torque may appear as a "knee" in the commanded torque graph of FIG. 10. However, the precise location of the knee may not be immediately clear. To facilitate identification of the end effector mutual engagement position, it is helpful to limit the analysis of the data to a limited range. The data may be restricted to a position range within which engagement is expected to occur, thereby assuming that the calibration offset will be within a predetermined range. For example, it may be assumed that the calibration offset for the end effector mutual engagement configuration will be between a nominal or initially commanded configuration of the jaws being open by 5 degrees (+5 degrees), and the jaws being squeezed past closed by 20 degrees (−20 degrees).

Figure 11:
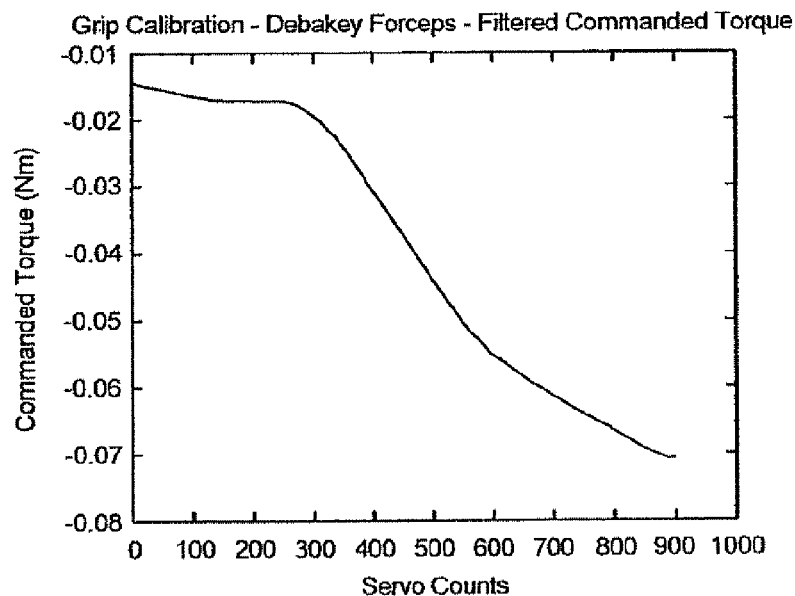
FIG. 11 graphically illustrates a relationship between commanded torque and servo counts as taken from the data of FIG. 10, in which the commanded torque has been filtered.
Figure 12A:
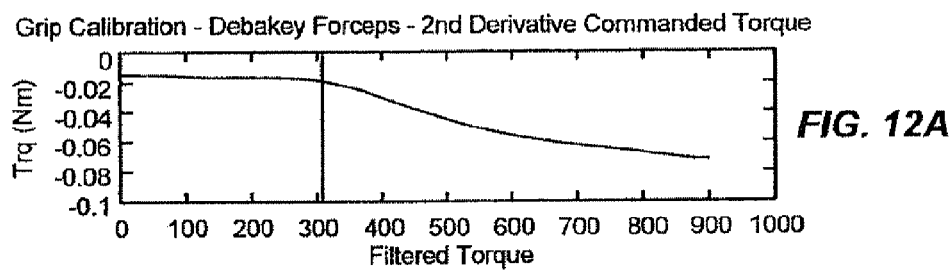
FIGS. 12A-12C graphically illustrate taking of a second derivative of the relationship illustrated in FIG. 11.
Figure 12B:
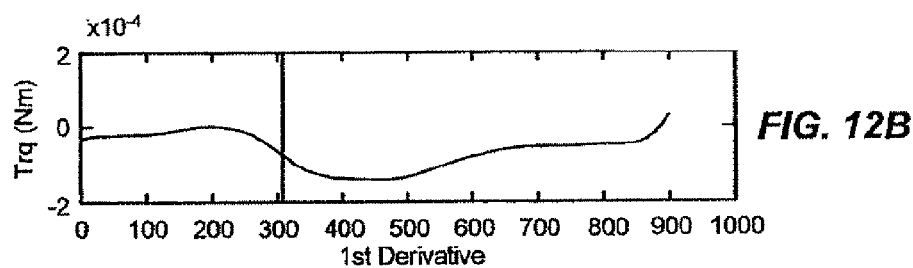
Figure 12C:
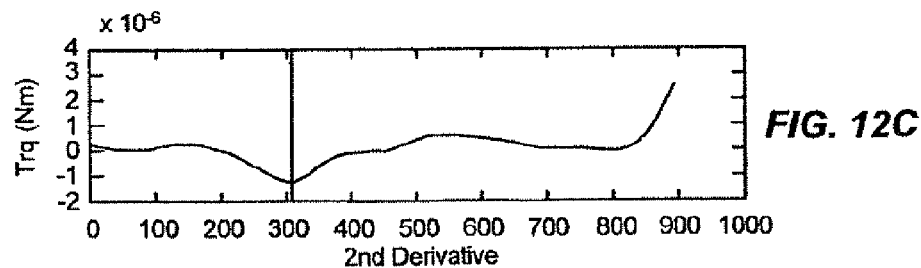
Figure 13:
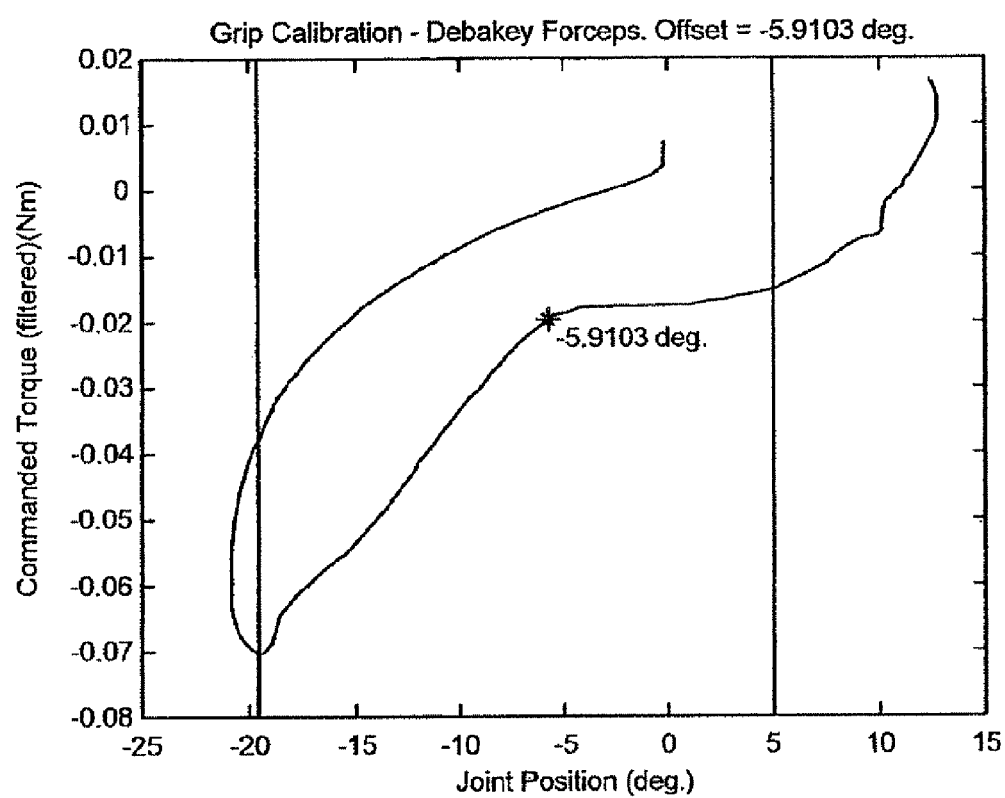
FIG. 13 graphically illustrates a relationship between commanded torque and joint position, and identifies an initial end effector engagement configuration at which the end effector elements are brought into mutual engagement.

The commanded torque plot of FIG. 10 may reflect variations in torque applied to compensate for friction in the manipulator, to enhance precision, and the like, as more fully described in U.S. Pat. No. 6,565,554. These commanded torques are effectively noise when determining grip calibration, with the noise primarily being at approximately the Nyquiest frequency, largely above the frequency of interest for calibration analysis. Hence, it may be helpful to include in processor 402 a filter to help identify the knee in the commanded torque draft. The filter may comprise a low pass filter, the exemplary filter comprising a 5 Hz low pass Butterworth filter, although other frequencies might also be used. The filtered commanded torque in the area of interest is illustrated in FIG. 11, showing the expected knee.

Referring now to FIGS. 11 and 12A-12C, the mutual engagement configuration of the end effector should correlate with the position of greatest curvature in the negative direction of the commanded torque data. This can be identified from the minima of the second derivative of the commanded torque. Once the mutual engagement configuration is known, calibration of the mounted tool can then be effected by applying a difference between the actual position and the commanded position of the end effectors as an offset to the grip controllers described above, for example, so that the closed configuration of the handle 226 (at which the handle members first engage the resilient bumper 60*a*) corresponds to the mutual engagement configuration of the end effectors. This difference can be stored as an offset in grip calibration data table 405 for the tool/manipulator combination.

Typically, grip calibration will take over a half a second to implement, often taking over a second, with the exemplary embodiment taking about 2 seconds. To avoid excessive delays during a procedure, processor 402 may store the grip calibration offset or other grip data in a memory of the processor, with the memory ideally storing a table of grip calibrations and instrument identifiers for each manipulator, so that the processor records each end effector/manipulator combination used during a surgical procedure. If an instrument has already been used during a procedure, the stored calibration may be used without repeating the grip calibration—if the mounted instrument has not previously been mounted on that particular manipulator during a procedure, the grip calibration will be performed. Grip calibration may be performed during data reading from and/or writing to information on the memory of the tool, which may occur when a tool is first used in each procedure.

Grip calibration may not determine an appropriate offset for a tool/manipulator combination for a variety of reasons, including a broken cable or failure of the tool interface to properly engage with the tool holder, a tool never reaching the commanded or mutual engagement configuration, and the like. For calibration failures, the grip calibration offset can be safely set to zero, so that the tool is assumed to be at the nominally commanded configuration, as the instruments may be inoperative (and hence will not be used anyway). By not storing data for calibration failures, the processor may treat the tool as not previously having been mounted on the manipulator, so that calibration can again be attempted.

Optionally, the grip calibration procedure may be deemed inappropriate for one or more tool types having two end effector elements. For example, although a clip applier as illustrated in FIG. 3D may benefit a grip calibration, such a calibration may actuate a clip prior to the clip reaching the target tissue. Hence, the processor may forego grip calibration in response to some tool type identifiers of such tools.

While the exemplary embodiments have been described in detail, for clarity of understanding and by way of example, a variety of changes, adaptations, and modifications will be obvious to those of skill in the art. Hence, the scope of the present invention is limited solely by the appended claims.

What is claimed is:
1. A system comprising:
   an input linkage comprising a first grip member movable relative to a second grip member;
   an end effector comprising a first end effector element movable relative to a second end effector element;
   a robotic arm transmitting a signal in response to mounting the end effector on the robotic arm; and
   a processor coupling the input linkage to the robotic arm, the processor configured to calibrate the mounted end effector in response to the signal by bringing the first and second end effector elements into mutual engagement;
   wherein the input linkage and the robotic arm each have a plurality of degrees of freedom, the processor effecting movement of the robotic arm in response to articulation of the input linkage;
   wherein, between mounting of the end effector and starting a surgical procedure using the end effector, the processor does not effect a calibration movement of any degree of freedom of the input linkage or the robotic arm other than said mutual engagement of the first and second end effector elements.

2. The system of claim 1, the robotic arm comprising at least one motor driving the end effector, wherein the processor comprises programming to calibrate the mounted end effector by:
   monitoring a commanded torque signal to the at least one motor;
   monitoring position of the first and second end effector elements; and
   identifying a change in the commanded torque signal versus the position of the first and second end effector elements.

3. The system of claim 2, wherein the processor comprises programming to:
   filter the commanded torque signal prior to identifying the change.

4. The system of claim 3, wherein the processor determines an end effector initial engagement configuration using a second derivative of the filtered commanded torque signal.

5. The system of claim 4, the processor configured to, during a surgical procedure, apply no additional torque to said at least one motor beyond a position of the end effector elements corresponding to the end effector initial engagement configuration.

6. The system of claim 4, wherein a feedback force is applied to the first and second grip members at a nominal closed position, and wherein the end effector initial engagement configuration corresponds to the nominal closed position.

7. The system of claim 6, wherein the first and second grip members comprise a biasing means for increasing resistance to gripping of the first and second grip members at the nominal closed position.

8. The system of claim 1, the processor further configured to calibrate the mounted end effector once per surgical procedure for each end effector mounted on the robotic arm.

9. The system of claim 1, the plurality of degrees of freedom of the input linkage comprising three orientational degrees of freedom of the first and second grip members, the plurality of degrees of freedom of the robotic arm comprising six degrees of freedom.

10. The system of claim 1, further comprising a single element end effector, wherein a single end effector signal is transmitted by the robotic arm when the single element end effector is mounted on the robotic arm, and wherein the processor does not calibrate the mounted end effector in response to the single end effector signal.

11. A method comprising:
mounting an end effector to a robotic arm movable in a plurality of degrees of freedom, the end effector comprising a first end effector element movable relative to a second end effector element;
calibrating the mounted end effector by moving at least one of the end effector elements so as to bring the end effector elements into mutual engagement, the calibrating being performed in response to the mounting of the end effector to the robotic arm;
moving a first grip member of a handle relative to a second grip member of the handle in response to gripping;
articulating the end effector elements so that the end effector elements move in correlation with the moving of the grip members of the handle; and
between the mounting the end effector and starting a surgical procedure using the end effector, not effecting a calibration movement of any degree of freedom of the robotic arm other than said calibrating the mounted end effector.

12. The method of claim 11, the calibrating further comprising:
transmitting a commanded torque signal to at least one motor of the robotic arm to move the end effector;
monitoring position of the first and second end effector elements relative to said commanded torque signal; and
identifying an end effector element initial engagement drive position from a change in relationship between the commanded torque signal and the position of the first and second end effector elements.

13. The method of claim 12, further comprising filtering the monitored position prior to the identifying.

14. The method of claim 12, wherein the identifying comprises determining a second derivative of the commanded torque signal versus the monitored position.

15. The method of claim 12, wherein the handle generates a feedback force at a nominal closed position of the handle, and wherein the identified end effector element initial engagement drive position corresponds to the nominal closed position of the handle.

16. The method of claim 15, further comprising increasing resistance to the moving the handle at the nominal closed position during a surgical procedure using the end effector.

17. The method of claim 11, further comprising removing the end effector from the robotic arm and mounting a second end effector having a single end effector element to the robotic arm, wherein a single element end effector signal is transmitted by the robotic arm when the second end effector is mounted thereon, and wherein no calibrating of the second end effector element is performed in response to the single element end effector signal.

* * * * *